United States Patent [19]

Tanouchi et al.

[11] Patent Number: 4,478,723
[45] Date of Patent: Oct. 23, 1984

[54] ADSORPTIVE SEPARATION METHOD

[75] Inventors: Masatoshi Tanouchi, Arcadia, Calif.; Hirshumi Akiyama, Nobeoka, Japan

[73] Assignee: Asahi Kasei Kogyo Kabushiki Kaisha, Osaka, Japan

[21] Appl. No.: 383,692

[22] Filed: Jun. 1, 1982

[30] Foreign Application Priority Data

Jun. 15, 1981 [JP] Japan ................................ 56-90841
Jun. 15, 1981 [JP] Japan ................................ 56-90840
Jul. 31, 1981 [JP] Japan ................................ 56-119321
Sep. 2, 1981 [JP] Japan ................................ 56-137071

[51] Int. Cl.$^3$ ............................................. B01D 15/00
[52] U.S. Cl. .................................... 210/674; 210/690; 585/805; 585/821; 585/828
[58] Field of Search ............................... 210/656–659, 210/672, 674, 690, 677; 585/805, 821, 825, 828

[56] References Cited

U.S. PATENT DOCUMENTS

| | | | |
|---|---|---|---|
| 2,985,580 | 5/1961 | Broughton et al. | 210/34 |
| 3,416,961 | 12/1968 | Mountfort et al. | 127/46 |
| 3,494,104 | 2/1970 | Royer | 55/67 |
| 4,022,637 | 5/1977 | Sutthoff et al. | 127/46 |
| 4,109,075 | 8/1978 | Deaton | 536/1 |
| 4,198,295 | 4/1980 | Vajna | 210/672 |

FOREIGN PATENT DOCUMENTS

| | | |
|---|---|---|
| 43-17643 | 7/1968 | Japan . |
| 46-24243 | 7/1971 | Japan . |
| 49-27569 | 7/1974 | Japan . |
| 2031013A | 8/1979 | United Kingdom . |

OTHER PUBLICATIONS

High-speed liquid chromatography (T. Kojima, Tokyo Kagaku Dojin, pp. 282–283 & 246–247, 1976) (L. R. Snyder and J. J. Kirkland, Introduction to Modern Liquid Chromatography, John Wiley & Sons, 1974).

Primary Examiner—Ivars Cintins
Attorney, Agent, or Firm—Armstrong, Nikaido, Marmelstein & Kubvocik

[57] ABSTRACT

An adsorptive separation method capable of effectively separating the desired component from a mixture containing the same at a high purity and a high recovery ratio, and easily coping with scale-up of the apparatus is disclosed. This method comprises alternately supplying a starting mixture A comprising a plurality of substances and a desorbent into a column packed with an adsorbent, treating to form and move an adsorption band of the starting mixture A and recovering the intended component at a purity higher than the aimed purity from an eluate, wherein after the entire amount of the intended component passing through the column is increased over the amount of the intended component in the starting mixture A and the intended component is separated and recovered, the portion B which is at least a part of the remaining intended component-containing portion, and in which the desorbent is separated and removed to a concentration lower than the desorbent concentration in the starting mixture A and the intended component is contained at a concentration higher than the concentration of the intended component in the starting mixture A is mixed with the starting material A and supplied to the column or said portion B and the starting mixture A are supplied to the column one by one, and then, the desorbent is supplied successively.

14 Claims, 29 Drawing Figures

ADSORPTIVE SEPARATION METHOD

BACKGROUND OF THE INVENTION

(1) Field of the Invention

The present invention relates to an adsorptive separation method for adsorbing and separating an intended component from a mixture comprising at least two substances at a purity higher than the aimed purity in an economically advantageous manner, which can easily cope with scale-up of the apparatus.

More particularly, the present invention relates to an adsorptive separation method in which a mixture comprising a plurality of substances and a desorbent are alternately supplied to a column packed with an adsorbent and while an adsorption band of the mixture of said substances is being formed and moved, the intended component is separated from the eluate portion at a purity higher than the aimed purity economically advantageously and which can easily cope with scale-up of the apparatus.

(2) Description of the Prior Art

As a method for separating and obtaining an intended component at a high purity from a mixture comprising a plurality of substances, there are known various methods such as the distillation separation method using a rectifying column, the low-temperature processing crystallization method and the solvent extraction method, and these methods are carried out on an industrial scale according to the properties of substances to be separated. Furthermore, industrialization of the adsorptive separation method using an adsorbent having a selective adsorbing capacity and a desorbent has recently been increased. The development of this adsorptive separation method is due to the fact that various adsorbents having a high selective adsorbing capacity have been developed and various adsorptive separation conditions for these adsorbents combined with desorbents have been created and also to the fact that the conditions for separating substances that cannot be separated according to the conventional methods have been revealed. There also is known a method in which components having a low relative volatility are rectified at a large stage number and a high reflux ratio. This method, however, is defective in that the consumption of steam is great and cannot cope with the recent increase of energy expenses As a method for solving this problem, the adsorptive separation method utilizing the selective adsorbing capacity is promising.

As the solid adsorbents now used on an industrial scale, there can be mentioned not only synthetic zeolites but also active carbon, silica gel, active alumina, ion exchange resins, polystyrene gel, clay, diatomaceous earth and porous glass. These solid adsorbents have inherent characteristics, respectively, and appropriate adsorbents should be selected according to the object of the separation operation while taking the adsorbing characteristics of the adsorbents, the properties of the starting mixtures and the lives and costs of the adsorbents into consideration. Recently, various designs of the micro- and macro-structures and various kinds of post-treatment (such as metal ion exchange and acid treatment) have been developed so as to improve these solid adsorbents for obtaining high selective adsorbing characteristics, and significant progress has been made in the field of solid adsorbents.

As the industrial process using a zeolite as an adsorbent, there are known the separation of n-parafins, the separation of n-olefins, the separation of butene-1, the separation of xylene, cymene and diethylbenzene isomers, the separation of cyclohexane from cyclohexene, the separation of -pinene and -pinene and the separation of fructose from glucose.

It is well-known that a so-called high performance liquid chromatography using high-capacity porous particles having a particle size of about 10 $\mu m$, such as Zipak®, Cerasil®, Perasil®, Sil® and Zorbax®, has recently been developed widely as a means effective for the separation of organic substances.

As another method for separating an intended component from a mixture comprising a plurality of substances, there is known a method using an ion exchange resin. For example, this method is utilized for the separation of fructose from glucose, the separation of rare earth metal ions, the separation of organic and inorganic acids and the separation of amino acids.

These methods for the adsorption and separation of mixtures comprising a plurality of substances by using solid adsorbents and liquid desorbents are included in the category of the technique called "liquid-solid column chromatography" in a broad sense. More specifically, when a liquid of a mixture is passed through a column (tower) packed with a solid adsorbent, the respective components of the mixture are distributed into the adsorbent side (stationary phase) and the moving liquid side (mobile phase) at different ratios according to the solid-liquid equilibrium relationship, that is, the difference in the adsorptive force, and therefore, the difference in the moving speed is brought about among the components of the mixture and separation is thus effected. The respective components thus separated are allowed to flow out from the downstream side of the column, and the effluent is continuously or intermittently analyzed to determine the concentrations of the components in the effluent and the fraction of the effluent containing the intended component is recovered.

In the case of the conventional adsorptive the separation technique according to the liquid chromatography, separation of the desired component from a mixture of inorganic or organic substances is ordinarily accomplished according to the following procedures:

(1) First, a mixture containing a substance to be separated and recovered is supplied as the starting mixture to a column (adsorption column) packed with an adsorbent (at this step, the mixture forms an adsorption band in the upstream portion of the column).

(2) Then, a desorbent is supplied to move the adsorption band downward (during this moving step, the respective components are gradually separated according to the difference in the adsorbing forces of the adsorbent for the respective components).

(3) The desorbent is further supplied to the column and the separated components are eluted from the column in sequence.

(4) The eluate fraction containing the intended component having the aimed purity is recovered.

(5) The desorbent in the eluate fraction is removed and the intended component is recovered.

In the foregoing manner, the mixture comprising a plurality of substances and the desorbent are alternately supplied into the column packed with the adsorbent, and the above procedures (1) through (5) are repeated, whereby the intended component is separated and recovered at the aimed purity. This method is widely adopted on an industrial scale.

This separation method, however, involves problems to be solved, which will now be described in detail with reference to an embodiment in which a mixture comprising a substance X for which the adsorbent has a weak adsorbing force and a substance Y for which the adsorbent has a strong adsorbing force is supplied in a column and the substance Y is separated as the intended component. Of course, this embodiment is given for facilitating the understanding.

The graph on which the change in the concentration of the component in the effluent at the outlet of the column according to the elution time (or the amount of the effluent) is plotted is called a "chromatogram". In the case where the adsorbing forces of the adsorbent to the substances X and Y do not greatly differ from each other or where the developing distance is short even if there is a great difference between the above adsorbing forces, the components X and Y are not completely separated (by the term "complete separation" is meant a state where both the components X and Y are not co-present), and the chromatogram curves of the components X and Y overlap each other and there is obtained an effluent in which both the components X and Y are co-present. For example, a chromatogram as typically shown in FIG. 1 is obtained. A long developing distance is required for attaining complete separation of these components X and Y. Accordingly, the scale of the adsorption column inevitably must be increased and therefore the method is not suitable for the practical operation. Furthermore, as the adsorption band moves in the column, the adsorption band is expanded and the concentration of the intended component is gradually reduced, with the result that the productivity of the adsorption column is reduced and the load on the separation of the intended component from the desorbent by distillation, extraction and recrystallization is increased. Therefore, complete separation is not always advantageous from an industrial viewpoint. In the actual operation, it often happens that the incorporation of the non-intended component (component X) into the intended component (component Y) is not practically disadvantageous if the concentration of the non-intended component is lower than the allowable concentration. In this case, complete separation of the components X and Y is not absolutely necessary. Accordingly, the method is advantageously carried out on an industrial scale only when for the economical reasons, for example, in view of the manufacturing costs and the cost of construction of installations such as columns, it is permissible to separate and recover the intended component without complete separation of the components X and Y.

In the case where a chromatogram as shown in FIG. 1 is obtained and the component Y is recovered at a purity of, for example, 90% (the component X is included as an impurity in an amount of 1/9 of the amount of the component Y), at the time ($t_1$) on the chromatogram, valves outside the column are changed over or another necessary operation is performed so that the effluent after the time ($t_1$), that is, the effluent in which the entire purity of the component Y is higher than 90%, is collected, and if the desorbent is removed from the effluent, the component Y having a purity higher than 90% can be obtained at a maximum recovery ratio. On the other hand, the effluent before the elution time ($t_1$) is discarded (the component Y contained in the hatched portion in FIG. 1 is lost), or this effluent is utilized again. For example, in the case of the separation of p-xylene from a mixture of xylene isomers, the effluent containing a smaller amount of p-xylene is distilled and then fed to the isomerization step to form p-xylene according to the chemical equilibrium, and the so-treated effluent is fed as the starting material to the chromatographical process again.

The problems involved in the above-mentioned conventional adsorptive separation method are summarized in the following two points:

(1) It is impossible to increase the recovery ratio without any economical sacrifice, and it is practically impossible to obtain a recovery ratio of 100%. A method for obtaining such a high recovery ratio is not optimal and the application range of this method is drastically limited, and in this case, the recovery ratio or purity is very low.

(2) The chromatogram is greatly changed (disturbed) due to scale-up of the apparatus, and a large-diameter absorption column cannot advantageously be utilized.

These two points will now be described in detail.

At first, the point (1) is discussed. As pointed out hereinbefore, when there is not a great difference between the adsorbabilities of the components X and Y, or when the developing distance is short even if there is a great difference between the adsorbabilities of the components X and Y, the components X and Y are not completely separated (by the term "complete separation" is meant the state where both the components X and Y are not co-present), and the chromatogram curves of the components X and Y overlap each other and there is obtained an effluent in which both the components X and Y are co-present. For example, a chromatogram as typically shown in FIG. 1 is obtained. A long developing distance is required for attaining complete separation of these components X and Y. Accordingly, the scale of the adsorption column is inevitably increased and the method is not suitable for the practical operation. Furthermore, as the adsorption band moves in the column, the adsorption band is expanded and the concentration of the intended component is gradually reduced, with the result that the productivity of the adsorption column is reduced and the load on the separation of the intended component from the desorbent by distillation, extraction and recrystallization is increased. Therefore, complete separation is not always advantageous from an industrial viewpoint. Accordingly, the adsorptive separation method is advantageously performed on an industrial scale only when for the economical reasons, for example, in view of the manufacturing costs and the cost of construction of installations such as column, it is permissible to separate and recover the intended component without complete separation of the components X and Y. In short, the application range of the method is limited.

In the conventional method, the following problem should be solved so as to obtain the intended component stably. As pointed out hereinbefore, a maximum recovery ratio (highest yield) can be obtained when collection of the effluent is started at the time ($t_1$) in FIG. 1 where the highest allowable concentration of the component X appears. If collection of the effluent is started at a point after the time ($t_1$), the recovery ratio is reduced. On the other hand, if collection of the effluent is started at a point before the time ($t_1$), the purity of the product Y becomes lower than the aimed purity and the recovered product cannot be used.

Namely, in the conventional method, if cutting is not effected precisely at the intended cutting time ($t_1$), the recovery ratio or the purity is reduced. Moreover, it is very difficult to determine the cutting point ($t_1$) before elution of the total amount of the component Y is completed. Accordingly, in the case where the conventional method is carried out on an industrial scale, predetermined amounts of the mixture and desorbent are alternately supplied precisely at constant flow rates into the column, and cutting is performed at the time ($t_1$) determined as the cycle of a certain time. However constant flow rates and feed amounts may be maintained, disturbances of chromatograms are considerably large when the method is carried out on an industrial scale. Because of not only these disturbances but also variations of the mixing ratio of the components X and Y and their amounts, it is very difficult to effect cutting precisely at the predetermined point even if highly advanced recent control units, high-precision valves, high-precision metering pumps and analyzing devices are thoroughly utilized.

Accordingly, it is necessary that the cutting point should be set so that a certain deviation in the cutting point has no influence on the purity of the product. Namely, a point on the right side of the point ($t_1$) in FIG. 1 should be set as the cutting point. However, from FIG. 1, it will readily be understood that this margin for the deviation will result in substantial reduction in the recovery ratio.

Ordinarily, if the cutting time is deviated by 1 second from the point ($t_1$), the purity or the recovery ratio is reduced by 0.1 to 10%, though this value differs to some extent according to the substance to be separated or the separation system.

In order to effect adsorptive separation economically advantageously, it is necessary to solve the foregoing problems. Needless to say, these problems should also be solved when a mixture comprising at least three components is treated.

The point (2) will now be discussed.

When industrialization of an adsorption column is intended, usually, an apparatus of a bench scale is first tested and the scale is then increased to a pilot apparatus and further to a commercial apparatus. From the principle of the adsorptive separation, scale-up of the adsorption column is ordinarily accomplished by increasing the diameter while the developing distance, that is, the length of the column, is kept constant. This increase of the column diameter results in the non-uniformity of the packing structure in the radial direction of the column or the non-uniformity of distribution or confluence of the fluid, and the degree of disturbance of the chromatogram at the outlet of the column is larger than in the small-diameter column.

In the case of a column customarily adopted for ordinary adsorptive separation where the column length is much larger than the column diameter, the disturbance of the chromatogram is often more influenced by the non-uniformity of the packing structure in the radial direction than by the non-uniformity of the distribution or confluence of the fluid. The change of the chromatogram due to scale-up of the column diameter is diagrammatically illustrated in FIG. 2.

In FIG. 2, solid lines indicate typical chromatograms obtained when a mixture of two components X and Y is subjected to the adsorptive separation in a small-diameter column, and broken lines indicate chromatograms obtained when in a large-diameter column packed with the same adsorbent at substantially the same pack density, development is carried out under the same adsorption conditions by using the same desorbent. Since the adsorption conditions are the same, the degree of separation of the components represented by the distance between the peaks does not greatly differ between the two cases, but in the case of the large-diameter column, since non-uniform streams of the fluid are gathered, the respective peaks become broad and the overlapping region of the peaks is increased, and the cutting position for obtaining the intended component Y at a predetermined purity is retreated to the point ($t'_1$) from the point ($t_1$). Accordingly, the recovery amount of the component Y in case of the large-diameter column, which corresponds to the area defined by A', B' and D', is much smaller than the recovery amount in the small-diameter column, which corresponds to the area defined by A, B, C and D. Therefore, scale-up results in economical disadvantages, and in an extreme case, scale-up becomes practically impossible.

For example, when p-xylene is adsorbed and separated from a mixture of xylene isomers by using a zeolite as the adsorbent, if the column diameter is smaller than 20 mm, a disturbance in the chromatogram due to channeling has no substantial influence on the recovery ratio, though the value differs to some extent according to the intended purity or kind of the substance to be separated. However, if the column diameter is larger than 20 mm, the recovery ratio is reduced according to the packing method and in an extreme case, the p-xylene recovery ratio is lower than $\frac{1}{3}$ of the recovery ratio attained when the column diameter is 20 mm or less. This reduction in the recovery ratio is especially significant when the column diameter exceeds 200 mm, and it sometimes happens that recovery of p-xylene at an aimed purity is impossible because of long tailing of the components other than p-xylene. This problem is serious when the column diameter is 5,000 to 6,000 mm as in the case of a commercial column. In this case, the separation cost is increased owing to a reduction in the recovery ratio, and furthermore, it becomes substantially impossible to practically carry out the separation process on an industrial scale.

Ordinarily, for minimizing this influence by scale-up, contrivances have been made only on the method for packing the adsorbent so as to uniformalize the packing structure of the adsorbent. Of course, it is necessary to uniformalize the packing structure as much as possible, but in the case of a column having a diameter larger than 200 mm, this uniformalization is limited and the packing structure is inferior in the packing uniformity more or less to the packing structure attainable in a column having a diameter smaller than 20 mm. Furthermore, as taught in many patent specifications, many labors are required for attaining the uniform packing according to the known packing methods.

Moreover, even if the packing structure is uniformalized to such an extent that no large and broad flow rate distribution is produced, in the case where the mass transfer rate to the point of adsorption of the adsorbent from the fluid is very slow, that is, in the case where the substance having a higher adsorbability is pushed out by the substance having a lower adsorbability, the channeling or disturbance is increased even by a slight flow rate distribution in the radial direction of the column. As is seen from the foregoing description, the problem of channeling in the large-diameter column is related to various factors, and this problem cannot be solved only by attainment of a uniform packing structure. However, it is necessary to establish a flow method not causing channeling and a separation process allowing a certain channeling.

As a method for moderating the foregoing defects of the conventional adsorptive separation method, there can be mentioned a technique using a simultaneous moving bed in the method for separating hydrocarbons by using zeolites (see Japanese patent publications No. 15681/67, No. 17643/68 and No. 24243/71).

According to this method, since the adsorbent and developing agent are supplied in a counter-current manner, a constant chromatographical curve can be obtained, and therefore, the component Y can be withdrawn continuously from the region where the component X is not incorporated. In other words, the problem (1) of the conventional method is solved by this method and the adsorptive separation can be performed stably while maintaining the recovery ratio substantially at 100%. However, this method is defective in that the apparatus and system to be used become very complicated and the construction costs are much greater than in the conventional method. Moreover, the problem (2) cannot be solved by this method at all. More specifically, the disturbance of the chromatogram due to channeling caused by scale-up of the column diameter cannot be prevented at all by this method. Accordingly, although a certain recovery ratio can be attained according to this method, the obtained chromatogram is inevitably considerably flat. Therefore, the amount used of the desorbent per unit amount of the intended component is drastically increased and the cost of the energy necessary for removing the desorbent from the intended component is increased. Furthermore, since the width of the chromatographical band is increased, the utilization efficiency of the column is reduced.

We made researches with a view to eliminating the foregoing defects of the known improved technique while retaining advantages, such as simplicity and expediency, of the conventional adsorptive separation method, and as a result, we have now completed the present invention described below.

It is therefore a primary object of the present invention to provide an improvement in the method comprising alternately supplying a starting mixture comprising a plurality of substances and a desorbent into a column packed with an adsorbent and recovering the desired component at a purity higher than the aimed purity from the eluate portion while forming and moving an adsorption band of the starting mixture, in which (1) the recovery ratio of the intended component is increased and the separation is accomplished more economically advantageously than in the conventional method, and (2) the disturbance of a chromatogram caused by scale-up of the column diameter is coped with by (A) providing a flow method capable of substantially preventing occurrence of the disturbance or (B) providing a system allowing a certain disturbance so that the recovery ratio is not substantially influenced by such disturbance.

SUMMARY OF THE INVENTION

The present invention provides an adsorptive separation method comprising alternately supplying a starting mixture A comprising a plurality of substances and a desorbent into a column packed with an adsorbent, treating to form and move an adsorption band of the starting mixture A and recovering the intended component at a purity higher than the aimed purity from an eluate, wherein after the entire amount of the intended component passing through the column is increased over the amount of the intended component in the starting mixture A and the intended component is separated and recovered, the portion B which is at least a part of the remaining intended component-containing portion and in which the adsorbent is separated and removed to a concentration lower than the desorbent concentration in the starting mixture A is mixed with the starting material A and supplied to the column or said portion B and the starting mixture A are supplied to the column one by one, and then, the desorbent is supplied successively.

BRIEF DESCRIPTION OF THE DRAWINGS

In FIG. 1, $t_1$ represents a cutting position for recovering the component Y at a certain elevated purity.

In FIG. 3, $t_3$ represents the cutting position for recovering the component Y at an aimed purity.

If the amount of the component Y is increased in the starting mixture according to the present invention, a chromatogram as indicated by the solid line is obtained. Incidentally, $t_2$ represents the cutting position for recovering the component Y in the same amount as the amount of the component Y recovered if cutting is effected at the point $t_3$ in the conventional method. In this case, as is seen from FIG. 3, the component X is not incorporated in the recovered component Y and the component Y can be recovered at a purity of 100%. In FIG. 3, $t_4$ indicates an example of the cutting point for obtaining the remaining component Y-containing portion. The portion B is obtained by removing the desorbent from the fraction recovered between $t_4$ and $t_2$ (or concenrrating this fraction to increase the adsorbate concentration to the level in the starting mixture).

FIG. 4a illustrates an embodiment where the component is recovered at a higher purity than in the conventional method though the recovery amount and recovery ratio are the same as those obtained in the conventional method. In FIG. 4a, $t_5$ represents the cutting position for recovering the component Y in the same amount as in the conventional method (FIG. 1) (the amount recovered after the point $t_2$ in FIG. 3), $t_6$ represents the cutting position where the amount of the portion B is the same as in FIG. 3, and $t_7$ represents the critical position for recovering the component Y at the aimed impurity.

FIG. 4b shows a chromatogram obtained in a preferred embodiment in which the entire amount of the component Y in the starting mixture A is recovered at a purity higher than the aimed purity. In FIG. 4b, $t'_5$ represents the point where the amount of the component Y accumulated from the rear end becomes equal to the amount of the component Y in the starting mixture A, that is, the component Y is recovered at a recovery ratio of 100%, and $t'_6$ represents the point where the amount of the component Y accumulated from the front end becomes equal to the amount of the component Y in the starting mixture A. The portion B is obtained between the points $t'_6$ and $t'_5$. Incidentally, $t_7$ is defined as in FIG. 4a.

In FIG. 6, $t_{10}$ represents the position of the substantially rear end of the component Y. The amount used of the fresh desorbent can be saved by the amount corresponding to the amount of the desorbent contained in the fraction between $t_9$ and $t_{10}$.

MX: m-xylene
OX: o-xylene
EB: ethylbenzene
PX: p-xylene
o-DEB: o-diethylbenzene
m-DEB: m-diethylbenzene
p-DEB: p-diethylbenzene
B: the portion obtained by reducing the concentration of the desorbent in the remaining intended component-containing portion left after recovery of the intended component, to a level lower than the desorbent concentration in the starting mixture
$B_1$ and $B_2$: fractions obtained by dividing the portion B into two parts, which are numbered as $B_1$ $B_2$ in the order of elution
C: the fraction of the tailing rear end portion of the chromatographic band, that is directly used again without reduction of the desorbent concentration
$t_F$: the elution time of the front end of the chromatographic band
$t_E$: the elution time of the rear end of the chromatographic band
$t_C$: the elution time for recovery of the intended component
$t_P$: the critical elution time for recovering the intended component at the aimed purity
$t_R$: the position for collecting the portion B
$t_M$: the position for dividing the portion B into two parts
$t_{Tail}$: the position for collecting the portion C
$\Delta t$: the margin of the cutting time for recovering the intended component at a purity higher than the aimed purity
$t_Q$: the elution time of the rear end of MX

DETAILED DESCRIPTION OF THE PREFERRED EMBODIMENTS

Figure 3:
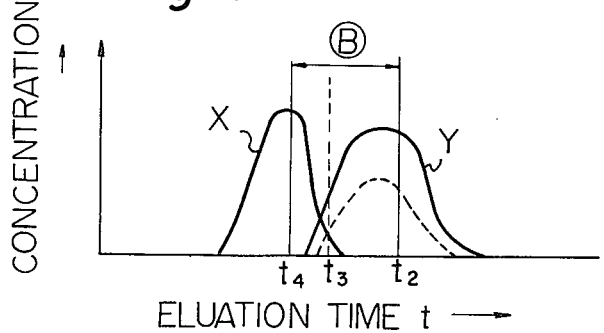
FIG. 3 shows a chromatogram illustrating the principle of the present invention. The components X and y are as defined in FIG. 1. The broken line indicates a chromatogram obtained in the conventional method.

The adsorptive separation method of the present invention will now be described with reference to the embodiment shown in FIGS. 1, 3, 4a and 4b where a mixture of two components X and Y is separated. According to the present invention, in the two-component system shown in FIG. 1, the intended component Y is mixed into the starting mixture of the components X and Y and is chromatographically developed preliminarily to obtain a chromatogram curve as shown in FIG. 3. In FIG. 3, the curve of the broken line is the chromatogram curve of the component shown in FIG. 1, which has been transferred from FIG. 1. In the chromatogram obtained according to the present invention, such as one shown in FIG. 3, the chromatographic curves of the components X and Y are changed according to the kinds and concentrations of the components X and Y and the adsorptive separation conditions. However, manifestation of the effects of the present invention is not hindered by these changes.

Figure 1:
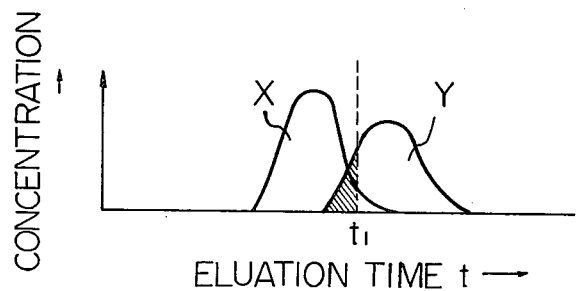
FIG. 1 shows chromatogram obtained in the conventional method where a mixture of two components X and Y is subjected to the adsorptive separation. The adsorbability of the component Y is higher than that of the component X.
Figure 2:
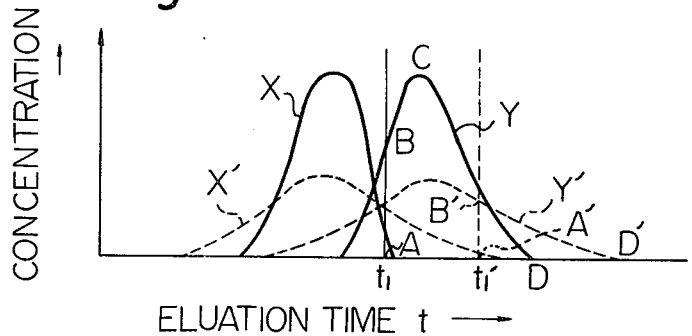
FIG. 2 shows the influences of scale-up of the column diameter in the conventional chromatographical separation method. The components X and Y are as defined in FIG. 1. In case of the small-diameter column, there is obtained a chromatogram indicated by solid lines where the cutting position is represented by $t_1$. If scale-up of the column is effected, the chromatogram is flattened as indicated by broken lines, and curves of the components X and Y are changed to X' and Y' and the cutting position is retreated to $t'_1$. Furthermore, the amount recovered of the component Y is drastically reduced to the area A', B' and D' defined by broken lines from the area A, B, C and D defined by solid lines, which is obtained in the small-diameter column.

In the chromatogram shown in FIG. 1, the aimed purity of the intended component is assumed to be 90%. In the chromatogram of FIG. 3 which is obtained according to the present invention, the position of the elution time for obtaining the same amount is indicated by $t_2$. In this newly obtained chromatogram, the elution time for recovering the component Y at a purity higher than 90% is indicated by $t_3$. Incidentally, the elution time $t_3$ appears more sooner than the elution time $t_2$, and the purity of the component Y obtained after the elution time $t_2$ is much higher than the purity of the component Y obtained after the elution time $t_1$ in FIG. 1.

Figure 4A:
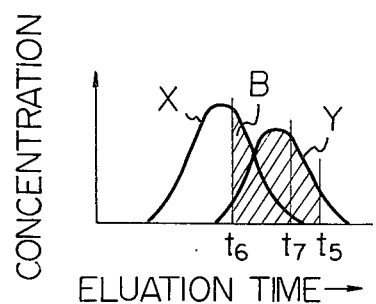
FIGS. 4a and 4b show examples of chromatograms obtained in the present invention by repeating the operations of the present invention according to the chromatogram shown in FIG. 3. The components X and y are as defined in FIG. 1.
Figure 4B:
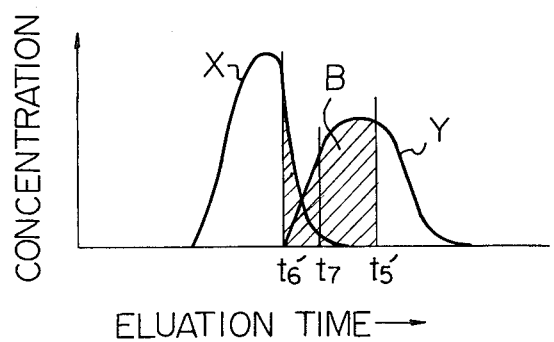

Then, the portion containing the component Y, which is collected from the portion left after recovery of the component Y at the position $t_2$, that is, the portion B obtained by reducing the concentration of the desorbent below the desorbent concentration in the starting mixture A in the fraction recovered between $t_4$ and $t_2$ it is preferred that the position $t_4$ be determined so that the ratio of the amount of the component Y to the amount of the component X in this fraction is higher than said ratio in the starting mixture A and all the remaining amount of the component Y is contained in this fraction, is mixed with the starting mixture A and the resulting mixture is supplied to the column, or the starting mixture A and the portion B are supplied into the column one by one, whereby a chromatogram as shown in FIG. 4a or 4b is obtained. In this chromatogram, for example, one shown in FIG. 4a, cutting is effected at the position $t_5$ necessary for obtaining the component Y contained in the starting mixture A, whereby the intended component Y is recovered, and the position $t_6$ for recovering the fresh portion B in the same amount as that of the portion B in FIG. 3 from the remaining intended component-containing portion is determined. The fraction before $t_6$ is cut and removed as a raffinate, and the fresh portion B obtained by reducing the concentration of desorbent below the desorbent concentration in the starting mixture A in the fraction recovered between $t_6$ and $t_5$ is mixed with the starting material A and the resulting mixture is supplied into the column or the starting mixture A and the fresh portion B are supplied into the column one by one. The foregoing procedures are repeated. Thus, the shape of the chromatogram becomes stationary and constant, and the state intended in the present invention is produced.

The operation efficiency in the method of the present invention can further be increased when a chromatogram as shown in FIG. 4b is obtained. Namely, in this case, the entire amount of the component Y contained in the starting material is recovered in the fraction collected after $t'_5$. This state can be attained by further increasing the amount of the component Y initially added to the starting mixture A or in a separation system in which the separation degree of the intended component is relatively good. In the embodiment shown in FIG. 4b, the fraction containing the component X in the same amount as the amount of the component X in the starting mixture A is cut at $t'_6$, raffinated and removed, the fraction after $t'_5$ is collected as the product extract, and the fraction between $t'_5$ and $t'_6$, after reducing the concentration of the desorbent below the desorbent concentration in the starting mixture A, is mixed as the fresh portion B with the starting mixture A. The resulting mixture is supplied into the column, or the starting mixture A and the fraction B are sequentially supplied into the column one by one. The foregoing procedures are then repeated. Thus, the shape of the chromatogram is stabilized and the intended component Y can be recovered at a purity higher than the aimed purity and a recovery ratio of 100%. In the embodiments shown in FIG. 4b, there is present a margin time between the point $t_7$ for attaining the aimed purity of the component Y and the point $t'_5$ for obtaining the component Y at a recovery ratio of 100%.

Conceptually, the chromatogram after establishment of the stationary state has a shape as shown in FIGS. 4a and 4b. Incidentally, $t_7$ represents the critical point for obtaining the component Y at the purity of 90%.

We found that the following effects are attained by the foregoing operations according to the present invention.

(1) In the fraction recovered after the point $t_5$ or $t'_5$ in FIG. 4a or 4b, the component A has a very high purity (the purity is substantially 100% in many cases), and the component Y can be recovered at a high recovery ratio.

(2) In the embodiment shown in FIG. 4b, there is produced a margin time between $t_7$ and $t_5$, and therefore, even if the position for cutting the intended component is deviated from $t_5$ to some extent, there is no risk of the reduction of the purity of the intended component. Furthermore, this deviation is automatically corrected according to the mechanism described below. More specifically, if cutting is effected before $t_2$, that is, if the component Y not to be recycled is collected in an amount larger than the amount of the component Y in the starting mixture, the amount of the component Y recycled is reduced, and, therefore, the new position $t_2$ is brought close to $t_3$ since the amount of the component Y is not changed. Ordinarily, this new position $t_2$ is brought close to only the cutting position but hardly goes beyond the cutting position to $t_3$. Even if the new position $t_2$ goes beyond the cutting position, that is, even if cutting is effected after $t_2$, automatic correction is performed so that $t_2$ is brought close to the cutting position.

When cutting is effected after $t_2$, that is, if the amount of the component Y not recycled is smaller than the amount of the component Y in the starting mixture A, since the amount of the component Y recycled is increased but the amount of the component Y in the starting mixture is not changed, the new position $t_2$ is separate from $t_3$ Ordinarily, this new position $t_2$ is only brought close to the cutting position but is hardly ever separated from $t_3$ beyond the cutting position. Even if the position $t_2$ goes beyond the cutting position, that is, if cutting is effected before $t_2$, as described above, automatic correction is performed so that the position $t_2$ is brought close to the cutting position.

If only the cutting position is set within a certain precision range (to such an extent that the position $t_2$ hardly goes beyond $t_3$), a margin time can always be maintained between $t_2$ and $t_3$, and the intended component can be recovered in an amount determined according to the separation system perpetually without fear of reduction of the purity of the product.

Furthermore, the precision in the determination of the cutting position need not be maintained at such a high level as required in the conventional method as shown in FIG. 1. Moreover, the intended component can be obtained at a high purity very stably. This is another great effect attained according to the present invention.

By virtue of the foregoing effects (1) and (2), the separation can be accomplished at a high recovery ratio and a high purity, and because of the margin for the automatic maintenance of the operation stability and the purity and recovery ratio, a certain disturbance of the chromatogram due to scale-up of the column diameter is rendered permissible without any economical sacrifice. In short, an adsorptive separation method in which a disturbance of the chromatogram due to scale-up can be allowed is provided according to the present invention.

(3) To our great suprise, it has been found that if the portion B containing the remaining component Y is supplied into the column again according to the method of the present invention, the state of the tail of the component X in the portion where the components X and Y overlap each other is highly improved and the rising of the chromatographic curve of the component X becomes sharp. It is construed that this phenomenon is due to the improvement of the dissociation force by increase of the amount of the component Y having a higher adsorbability than that of the component X, that is, the increase of the self-sharpening tendency in the boundary interface of the components in the adsorptive separation [see, for example, Funakubo et al., Kogyo Kagaku Zassi 64, (1), 167 (1961)]. This effect is an inherent effect of the present invention in which the adsorptive separation is carried out by increasing the amount of the component Y. By virtue of this effect, the most serious disadvantage in the high-efficiency separation, that is, intrusion of the preceding component into the intended component can be controlled to a minimum level.

Furthermore, the slow mass transfer rate of the substance between the point of the adsorbent and the fluid, which promotes the disturbance due to the non-uniform structure of the packed layer even to an irredeemable level, can be increased by the above-mentioned self-sharpening effect and the moving speed can be increased. Accordingly, the disturbance due to the non-uniform structure of the packed layer results only in generation of a flow speed distribution and this disturbance per se is not promoted at all. Therefore, if only a certain uniformity is maintained in the packed layer structure, the disturbance of the chromatogram can be controlled within an allowable range. In short, a flow method for the chromatographic separation in which the disturbance is hardly caused can be realized very simply according to the present invention.

The foregoing effects (1), (2) and (3) are very significant for realizing scale-up of the column diameter of carrying out the adsorption on an industrial and commercial scale. For example, in the case where the scale of the column diameter is increased to 20 mm from 8 mm in the adsorptive separation of p-xylene from a mixture of xylene isomers by using a zeolite, in the conventional method, the recovery ratio $R_{99.5}$ of p-xylene having a purity of 99.5% is reduced to about 60% from about 90% by this scale-up. In contrast, according to the present invention, the recovery ratio $R_{99.5}$ can be maintained at a high level in each column. The reason is that intrusion of the preceding component, that is, ethylbenzene, into p-xylene can be controlled and a certain disturbance is compensated by the above-mentioned margin, with the result that a reduction in the recovery ratio by scale-up of the column diameter can effectively be prevented.

(4) If the chromatographic separation is carried out by increasing the amounts of the components over the amounts in the starting mixture as in the method of the present invention, it is considered that this ordinarily will result in expansion of the band width and reduction of the utilization efficiency of the column. However, if the increase in the amounts of the components is within such a range that the effects of the present invention can be attained, the peak heights are increased and the head portion becomes flat though it is indefinite whether or not the reason for this is that the amounts of the adsorbates exceed (overload) the adsorbing capacity of the adsorbent, but no substantial expansion of the band widht is observed at all. On the contrary, the region occupied by the adsorbates in the chromatogram is drastically increased and therefore, the amount of the desorbent used can be reduced and the energy required for removal of the desorbent by distillation or the like can be reduced drastically.

The technical contents of the present invention will now be described in detail.

By the term "mixture comprising a plurality of substances" used in the present invention is meant a mixture of inorganic and/or organic substances, and the kind of substances is not particularly critical. The inorganic substance mixture includes a mixture of metal ions such as transition metal ions, rare earth metal ions and alkali metal ions. All of the ordinary organic compounds are included in the organic substance referred to in the present invention. For example, there can be mentioned paraffinic, olefinic and aromatic hydrocarbons, alcohols, ketones, carboxylic acids, amines, nitro compounds, and their derivatives and polymers. In short, the substances that are separated according to the present invention are not limited to specific compounds. Furthermore, mixtures of organic and inorganic substances, for example, a mixture of hydrochloric acid and acetic acid and a mixture of an organic acid and sodium chloride, may be treated according to the method of the present invention. In short, all the organic substances to be separated by means of the chromatographic separation are included.

However, in order to attain the effects of the present invention at a highest efficiency, it is preferred that the mixture be substantially free of a desorbent. Namely, if the mixture does not contain a desorbent, that is, if the entire chronatographic band is not diluted with the desorbent, the self-sharpening effect of the present invention in the boundary between the components is especially significant, and the resistance to disturbance due to scale-up of the column diameter is highly increased as compared with the resistance to disturbance in the conventional method.

As the solid adosrbent that is used in the present invention, there can be mentioned synthetic zeolites, active carbon, silica gel, active alumina, ion exchange resins and polystyrene gel. The desorbent can optionally be selected among alcohols, amines, chlorine compounds, aromatic compounds, ether compounds and the like.

For separating the desorbent from the effluent fraction, there can be employed known methods such as distillation, cryogenic separation and extraction separation. A desorbent that can be separated by distillation is preferred.

All the systems of the adsorbent and desorbent that can be used for separation according to the substances to be separated can be utilized in the present invention. However, needless to say, the present invention need not be applied to a mixture of components that can be easily and completely separated from each other.

The amount increased of the intended component to be passed through the column is changed according to the kinds and compositions of the starting mixture and the intended component and the kind of the separation system. If this amount is excessively increased, the width of the chromatographic band is increased and the utilization efficiency of the column is reduced. In contrast, if this amount is too small, the effects of the present invention are reduced. Accordingly, the optimal amount increased should be determined according to the intended separation system. For example, when p-xylene is separted from a mixture of xylene isomers by using a zeolite, it is preferred that the amount of p-xylene be increased by 50 to 250% based on the amount of p-xylene in the starting mixture.

The intended component to be used for increase of the amount of the intended component may be one obtained in the chromatography shown in FIG. 1, or the component Y prepared separately may be added. In many industrial separation systems, components A can ordinarily only at the start of the adsorptive separation, and once the adsorptive separation is started, this additional amount of component Y is supplied by the portion B from the formed chromatogram and no practical trouble or disadvantage is brought about.

It is preferred that the portion B be determined so that all the remaining indended component is included in the portion B, because intrusion of the intended component into the raffinate can be inhibited. However, if this method is adopted, when the intended component is lengthily dispersed in the remaining portion, a large quantity of the fraction having a low concentration of the intened component should be supplied, resulting in reduction of the effects of the present invention. Accordingly, in this case, only a high-concentration part is preferably supplied.

In order to avoid the above-mentioned ineffective supplying, it is important to determine the portion B so that components other than the intended components are not included in large amounts.

The proportion of the remaining portion B to be supplied one by one subsequently to the starting mixture differs according to the separation system, but if the separation system is determined, this proportion can easily be determined.

In the present invention, there may be adopted a method in which the portion B is mixed with the starting mixture A and the resulting mixture is fed to the column, or a method in which the starting mixture A and the portion B are fed to the column one by one.

However, reduction of the concentration of the intended component by mixing the portion B, which has passed through the column and in which the concentration of the intended component has been increased over the level in the starting mixture, with the starting mixture is not advantageous, and the sequential feed method is preferably adopted if the sequential feed method is possible. In this case, if the adsorbability of the intended component is higher than that of the remaining component, that is, if the component Y in FIG. 1 is the intended component, it is preferred that the mixture A be supplied first and the portion B be supplied next. In contrast, if the adsorbability of the intended component is lower than that of the remaining component, that is, if the component X in FIG. 1 is the intended component, it is preferred that the portion B be fed first and the starting mixture A be supplied next. In order to shorten the distance of the unnecessary movement of the band at the developing step, it is preferred that the above-mentioned order of the feeding be adopted.

There may also be adopted a method in which the portion B containing the remaining intended component is divided into at least two parts and these parts are supplied in the order of elution. This method is very effective for enhancing the effects of the present invention. More specifically, the portion B is collected in the form of at least two fractions (divisions) and they are subjected to the desorbent-removing operation.

If the divided fractions are fed in the order of elution, the curve of the component other than the intended component rises very sharply in the region where it overlaps the curve of the intended component. Namely, the degree of separation between the components X and Y is greatly increased. Accordingly, the above-mentioned effects of the present invention are further enhanced. Ordinarily, the larger the number of the divided parts is, the sharper the rising of the above-mentioned curve is. However, if the number of the divided parts is increased, the trouble for changing over valves or the like is increased. Therefore, excessive increase of the division number is not advantageous. Ordinarily, if the portion B is divided into 2 or 3 parts, the attainment of the effects of the present invention is enhanced.

In other separation systems, it sometimes happens that if the portion B containing the remaining intended component is further finely divided, for example, into 3 to 5 parts and there is adopted a method in which some of the divided parts are fed before the starting mixture and the remaining parts are fed after the starting mixture, the entire band length is shortened and hence, the entire concentration of the intended component can be increased. This method is advantageous for decreasing the cost of separation of the desorbent at the step of collecting the intended component, though it cannot be said that this method can be applied to all the separation systems. Furthermore, in case of a separation system in which tailing of the intended component takes place, if the above-mentioned dividing method is carried out so that adjacent chromatographic bands overlap each other, the entire load for separation of the desorbent can be reduced. Furthermore, if the band length in the column is shortened according to the above-mentioned dividing method, the productivity of the column can be increased. There merits are especially significant in the case of a separation system comprising at least 3 components, for example, the separation system where p-xylene is separated from a mixture of xylene isomers by using a zeolite as the adsorbent.

As the embodiment for enhancing the effect of reducing the amount of the desorbent used, which is one of the main effects of the present invention, and obtaining better separation results as a whole, there can be mentioned a method in which the portion B is mixed with the starting mixture A and the resulting mixture is fed to the column or the starting mixture A and the portion B are fed to the column one by one, and then, the desorbent is supplied while controlling the amount of the desorbent so that the front and portion and/or the rear end portion of the adsorption band in which the concentration of the intended component is low is overlapped on the adjacent adsorption band after movement of a predetermined distance. Even if there is obtained a separation system in which the concentration of the intended component as a whole is sifficiently high, according to the kinds of the adsorbent and desorbent and the operation conditions, there often takes place a so-called leading phenonomen in which the long front end portion of the chromatographic band flows at a low concentration of the intended component or a so-called tailing phenomenon in which the long rear end portion of the band continues at a low concentration of the intended component. In order to obtaine the intended component form such low-concentration portion, a large quantity of the desorbent should be separated, which results in economical disadvantages.

The relative adsorption capacity ratio (selectivity) $K_Y^{RS}$ of the desorbent to the intended component to be separated is represented by the following formula:

$$K_Y^{RS} = \frac{\frac{\text{concentration of desorbent}}{\text{in adsorbent at equilibrium}}}{\frac{\text{concentration of desorbent}}{\text{in solution at equilibrium}}} $$

In order to perform the separation economically advantageously, it is preferred that the vale $K_Y^{RS}$ of the separation system be within a certain range. For example, in a separation system in which the adsorption band of the intended component comes behind and the value $K_Y^{RS}$ is much smaller than 1, tailing of the intended component is observed. In contrast, in a separation system in which the adsorption band of the intended component comes forward and the value $K_Y^{RS}$ is much larger than 1, there is observed a leading phenomenon in which the front end portion of the chromatographic curve is expanded forward. The value $K_Y^{RS}$ in such separation system depends on the concentration of the desorbent present in the system, and the higher the concentration of the desorbent is, the more violent tailing of the rear portion is.

In a system in which the above-mentioned leading or tailing is vigorous, in order to recover the intended component from such portion, it is necessary to separate and remove a large quantity of the desorbent.

Figure 5:
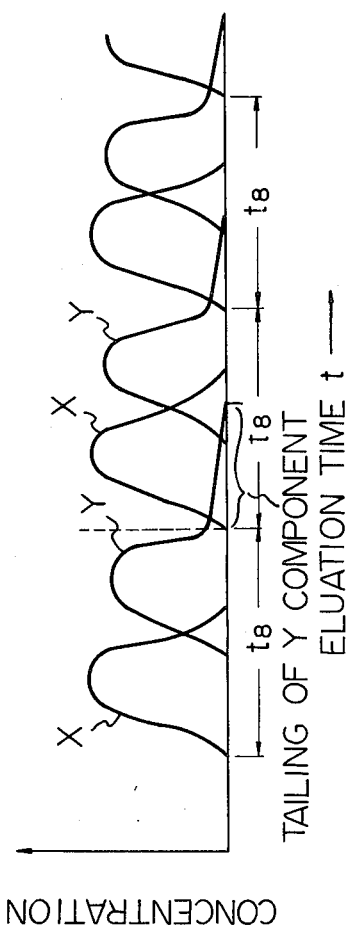
FIG. 5 shows a preferred embodiment of the present invention, in which in performing the chromatographic separation by alternately supplying the adsorbate comprising the starting mixture A and the portion B and the desorbent, the amount of the desorbent is adjusted so that the rear tailing end of the preceding chromatographic band where the concentration of the component Y is low is overlapped on the front end of the subsequent band. The band width is shortened by one cycle corresponding to the overlap and the band ends at $t_8$. This embodiment is advantageous in that the amount of the desorbent in the tailing portion of the component Y can be reduced and the utilization efficiency of the column can be increased by shortening the band width.

We made researches with a view to solving this problem, and as a result, we found that even if chromatographic development is carried out so that the tailing or leading region of the chromatographic curve overlaps with the adjacent chromatographic curve, no large deviation of the chromatographic curve is caused. If this embodiment is adopted, the economical advantages due to the above effects of the present invention are further increased. This embodiment in which the problem of tailing is solved is illustrated in FIG. 5. The position at which the rear or front end portion overlaps with the adjacent adsorption band is not simply determined, because the influence of overlapping on the separation differs according to the separation system. For example, however, in the case of the system of separating p-xylene from a mixture of xylene isomers by using a zeolite, especially good results are obtained when the fraction of the tailing portion of p-xylene in which the concentration of p-xylene is as low as 10 to 15% by weight or less overlaps with the adjacent adsorption band. If a portion having a higher concentration overlaps with the adjacent adsorption band, the separating effect is reduced or the disturbance of the chromatographic curve becomes vigorous. Overlapping of a certain cycle with the subsequent cycle at the tailing portion or the leading portion is accomplished by controlling the time of supplying the desorbent between two adjacent bands of the mixture to be separated in the column.

Figure 6:
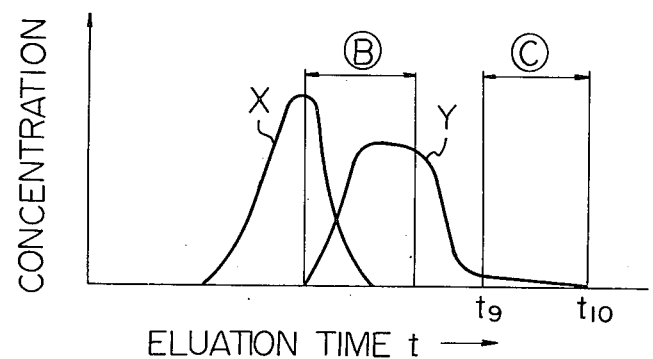
FIG. 6 shows another preferred embodiment of the present invention, in which the tailing portion of the component Y is cut at $t_9$ and the fraction between $t_9$ and $t_{10}$ is used again as the portion C together with the portion B without removal or concentration of the solvent.

As another embodiment for attaining the effect of reducing the amount of the desorbent used as in the above-mentioned embodiment, there can be mentioned a method in which collection of the intended component is performed so that the portion C containing the intended component at a relatively low concentration is not included in the collected fraction, and this portion C is supplied before or after the adsorbate portion comprising the starting mixture A and the portion B contiguously thereto. FIG. 6 illustrates this embodiment in which the problem of tailing of the component Y is solved. In this embodiment, the fraction C between $t_9$ and $t_{10}$ in which the concentration of the intended component is very low is returned to the feed zone of the column while the desorbent is contained therein, and the fraction C is used for the development contiguously to the adsorbate portion while attainment of an effect similar to the effect of the desorbent is expected and the intended component contained in this fraction C is not lost at all. Supply of the fresh desorbent in an amount corresponding to the amount of this fraction C becomes unnecessary. Accordingly, in this embodiment, the amount of the desorbent used and hence, the energy cost for separation of the desorbent can be reduced.

Ordinarily, the point where the concentration of the component Y is substantially zero is selected as $t_{10}$. In the case where low-concentration tailing continues for a long time, if the portion where the concentration of the intended component is very low overlaps with the adjacent adsorption band and the front end of the adjacent band is set as $t_{10}$, the band width can substantially be narrowed, and in this case, the utilization efficiency of the column can be increased significantly. In this case, the overlapping position differs according to the kind of the separation system and the required utilization efficiency of the column, but ordinarily, from the viewpoint of the utilization efficiency of the column, it is preferred that the fraction where the concentration of the intended component is lower than 1% should not be included in the fraction C but be overlapped on the adjacent adsorption band. Furthermore, it is preferred that the position $t_9$ be determined so that when the fraction C is used as the desorbent, the concentration of the component Y in the fraction C has not any bad influences on the separation state of the adsorbate portion comprising the starting mixture A and the portion B. For example, in the system of separating p-xylene from a mixture of xylene isomers by using a zeolite, it is preferred that the concentration of the component Y in the fraction C be 1 to 5% by weight. If the concentration is too high and exceeds this range, the degree of separation of the intended component is reduced or the band width is increased. If the concentration is below the above range, the effect of reducing the amount of the desorbent used in this embodiment is reduced.

The foregoing embodiments may similarily be applied to the case where the problem of leading of the component X having a low adsorbability arises. In the case where the problem of leading of the component X having a low adsorbability arises and the leading portion of the component X is treated as the fraction C, it is preferred that the fraction C be supplied after the adsorbate portion D comprising the fraction B and the starting mixture A contiguously to the portion D. If the fraction C is supplied before the portion D, since the adsorbability of the component X in the fraction C is low, the component X in the fraction C is kept ahead of the component X contained in the portion D and leading of the component X is readily rendered vigorous.

In the case where the problem of tailing of the substance Y having a high adsorbability arises and the tailing portion of the component Y is treated as the fraction C, it is preferred that the fraction C be supplied before the portion D contiguously thereto. If the fraction C is supplied after the portion D, since the component Y in the fraction C has a high adsorbability, the component Y in the fraction C moves in the column behind the component Y contained in the portion D, and therefore, tailing of the component Y is readily rendered vigorous.

Even in the case where the fraction C is supplied in the above-mentioned preferred sequence, if the fraction C is not contiguous to the portion D but the desorbent is interposed therebetween, since inclusion of the component X or Y in the fraction C into the portion D is hardly advanced during the development, tailing of the component X or leading of the component Y is likely to occur afresh and no good results can be obtained.

In the present embodiment, the fraction C is effectively utilized as the desorbent in the above-mentioned manner and the amount of the desorbent used can effectively be reduced. It is determined according to the characteristics of the treatment and the desired effect whether the method of the present embodiment or the method L of the foregoing embodiment where the fraction C overlaps with the adjacent band should be selected. In the overlapping method L, the amount of the desorbent used can be reduced by the amount corresponding to the overlap portion and the band width can proportionally be shortened, and the effect of increasing the utilization efficiency of the column is very high. However, it is impossible to directly recover the intended component contained in the tailing or leading portion which overlaps with the adjacent band. However, this loss of the intended component has no significant influences on the overall recovery ratio if there is an appropriate raffinate-recovering system. For example, in the system for separating p-xylene from a mixture of xylene isomers, the raffinate left after collection of the intended component and removal of the portion B is fed to the column during the isomerization step after removal of the desorbent and is subjected to the isomerization reaction to form the intended component afresh, and the so-formed intended component is included in the starting mixture A. Accordingly, the loss of the intended component is nothing but a loss by the side reaction during the isomerization process, and this loss is not significant. Therefore, the method L can be effectively adopted if there is such a raffinate-recovering system. However, if there is not such raffinate-recovering system, adoption of the method L is not preferred because the above loss is not compensated for at all.

In the method M in which the fraction C is utilized as the desorbent, even if the intended component is contained in the fraction C, since the fraction C is fed to the column again, no substantial loss of the intended component is caused. However, since the fraction C should inevitably the maintained at the development, the band width is longer by a distance corresponding to the fraction C than the band width in the method L, and therefore, the utilization efficiency of the column is lower than in the method L.

In the actual operation, the methods L and M may effectively be combined together. For example, in the system of separating p-xylene from a mixture of xylene isomers, a part of the tailing portion of p-xylene where the concentration of p-xylene is lower than 1% by weight overlaps with the subsequent adsorption band according to the method L and the overlap point is set as $t_{10}$, and in the remaining part of the tailing portion, $t_9$ is set at the point where the p-xylene concentration is 1 to 5% by weight and the fraction between $t_9$ and $t_{10}$ is used as the fraction C and fed before the portion D comprising the xylene isomer mixture A and the portion B contiguously thereto according to the method M. In this case, very good results can be obtained.

The size of the column to be applied to the method of the present invention is not particularly critical. However, since the adaptability of the present invention to scale-up of the column diameter is very high and high is one of the important effects of the present invention, when the column has a certain large diameter, the difference of the present invention over the conventional method become prominent.

A minimum diameter of a column of a bench scale is ordinarily about 2 to about 20 mm. In this case, the adsorption column is different from, for example, the high performance liquid chromatographic analysis apparatus in which an adsorbent having a very fine particle size is employed in the point that if the column diameter is in the above-mentioned range, the non-uniformity of the packed layer structure does not cause any serious problem, and any particular attention need not be paid to the method for packing the adsorbent. However, if the inner diameter of the column is increased beyond 20 mm and the ratio of the column diameter to the particle size of the adsorbent exceeds 20, the difference of the packed layer structure due to the difference of the packing method becomes prominent and has serious influences on the results of the separation. In particular cases, it sometimes happens that the recovery ratio at the aimed purity is reduced to ⅓ if the packing method is changed. This difference becomes more significant if the inner diameter of the column exceeds 200 mm, and it sometimes is rendered impossible because of the non-uniformity of the packed layer structure due to scale-up of the column diameter to substantially recover the intended component at the aimed purity. The problems to be encountered in industrializing the adsorptive separation method which has been found effective at the bench-scale experiment have already be described with reference to the conventional method, and in order to successfully industrialize this adsorptive separation method, it is very important to solve these problems. According to the present invention, as is seen from the foregoing description, these problems to be encountered in scale-up of the column diameter can effectively be solved. If this fact is taken into consideration, it may be said that the characteristic feature of the present invention are most effectively manifested when the inner diameter of the column is larger than 20 mm, especially larger than 200 mm, and the ratio of the column diameter to the particle size of the adsorbent is at least 20.

As the adsorptive separation process in which the method of the present invention is effectively utilized, there may be considered separation processes described hereinbefore with reference to the prior art. However, as the process in which the characteristic features of the present invention, such as the use of a starting mixture substantially free of the desorbent, reduction of the bend width by increasing the amount of the intended component over the amount of the intended component contained in the starting mixture and reduction of the amount of the desorbent used by increasing the amount of the intended component so that the head portion of the adsorption peak of the intended component is flattened, are effectively manifested and utilized, there can be mentioned a process in which a hydrocarbon mixture is adsorbed and separated by using a zeolite, and as the process in which the highest effects can be attained, there can be mentioned the process, referred to here and there in this specification, in which p-xylene is separated from a mixture of xylene isomers by using a zeolite, especially a faujasite type zeolite.

In this especially preferred separation process, it is preferred that a desorbent in which the ratio of the adsorbability of the desorbent to the adsorbent to the adsorbability of p-xylene, that is, the value $K_{PX}^{RS}$ (in which RS designates the desorbent and PX designates p-xylene) represented by the following formula, is in the range of from 0.3 to 3 be used:

$$K_{PX}^{RS} = \frac{\dfrac{\text{concentration of desorbent in adsorbent at equilibrium}}{\text{concentration of desorbent in solution at equilibrium}}}{\dfrac{\text{concentration of p-xylene in adsorbent at equilibrium}}{\text{concentration of p-xylene in solution at equilibrium}}}$$

Incidentally, the above value is one measured in a desorbent/$C_8$ isomers mixture system in which the desorbent is present in an amount of 10 to 90%.

When a lower aliphatic ether represented by the following general formula:

$$R_1-O-R_2$$

wherein $R_1$ and $R_2$, which may be the same or different, stand for an alkyl group having 3 to 5 carbon atoms, exclusive of an n-butyl group,
such as n-propyl ether, isopropyl ether, sec-butyl ether or tert-butyl ether, is used as the desorbent, an especially good chromatogram is obtained, and the present invention can be applied to the above adsorptive separation process most effectively.

According to the present invention, the following effects can be attained and the problems to be encountered in industrialization of the adsorptive separation process can be solved completely.

(1) The intended component can be recovered at a high purity and a high recovery ratio.

(2) The purity and recovery ratio can be stably maintained at certain levels by the automatic correcting function.

(3) Even if the chromatogram is disturbed to some extent by scale-up of the column diameter or the like, the purity and recovery ratio can be maintained at relatively high levels and the allowable range of this disturbance is relatively broad.

(4) The disturbance of the chromatogram by the non-uniformity of the flow in the packed zone, which is due to scale-up of the column diameter, can be controlled to a minimum level.

(5) The quantity of energy necessary for separating the desorbent from the intended component can be reduced.

(6) The amount of the adsorbent used per unit amount of the recovered intended component, that is, the utilization efficiency of the column, can be increased.

(7) Since the method includes only batchwise operations which are simply repeated, the apparatus structure can be simplified.

Accordingly, the present invention makes great contributions to the art.

The present invention will now be described in detail with reference to the following Examples that by no means limit the scope of the invention.

The present invention will now be specifically illustrated by, but is by no means limited to, the Examples set forth below in which all percentages are expressed on a weight basis unless otherwise specified.

Example 1 (Comparative)

Four stainless steel cylindrical columns each provided with a jacket and liquid distributors and liquid gathering collectors at the top and bottom thereof, and each having an inner diameter of 8 mm and a length of 2.5 m were connected in series with stainless steel pipes each having an inner diameter of 1 mm to provide a chromatographic separation column. The columns were packed with a potassium ion exchanged X type zeolite having a particle size of 60 to 100 meshes. The columns were stabilized at a temperature of 120° C. and, then, a desorbent, furan was charged to the columns to condition the packing in the columns. Then, 50 cc (corresponding to 0.17 cc/unit weight of the packing) of a starting mixture A (a so-called mixed xylenes) to be separated in this column containing 15% of p-xylene (hereinafter referred to as "PX"), 20% of ethylbenzene (hereinafter referred to as "EB"), 45% of m-xylene (hereinafter referred to as "MX") and 20% of o-xylene (hereinafter referred to as "OX") was downwardly charged to the column by a constant rate pump. Thus, an adsorption band was formed. Subsequently, the desorbent was downwardly charged to the column at a flow rate of 9.5 cc/min, thereby developing the above-mentioned adsorption band. Eluates discharged from the bottom of the column were collected as fractions at intervals of 30 seconds. Each fraction was quantitatively determined by a gas chromatographical analysis device to obtain weight concentrations of the starting components and the desorbent in each sample.

Figure 7:
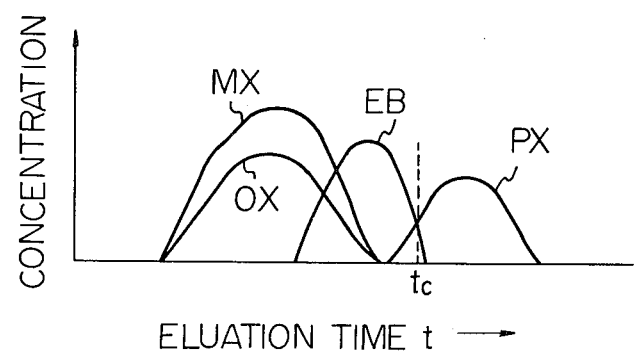
FIGS. 7 through 23 are chromatograms illustrating the contents of the Examples of the present invention. Conditions for obtaining these chromatograms are described in detail in the Examples and Table 1. Symbols in these Figures have the following meanings.

The results are shown in a chromatogram of FIG. 7 in which the abscissa axis represents a time from the initiation of the charge and the development and the ordinate axis represents the concentration of each adsorbed component. As a result of the chromatogram, it was found that the purity of the intended component PX was 99.5% and the elution time tp thereof was 33.1 min.

The time at $t_p$ was fixed and the separation operations were repeated. The recovery yields of the intended component in the starting mixture A and the purities of the recovered intended component were changed as shown in Table 1 below. The average recovery amount of the desired component was 1.5 g.

Example 2

Figure 8:
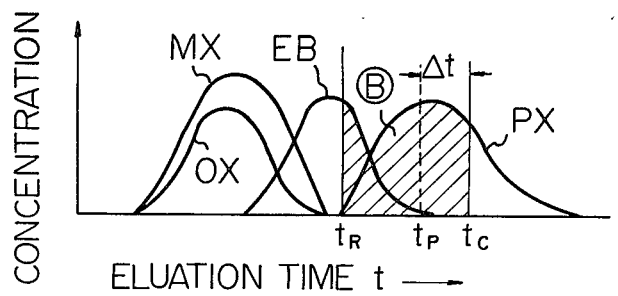
Figure 8:
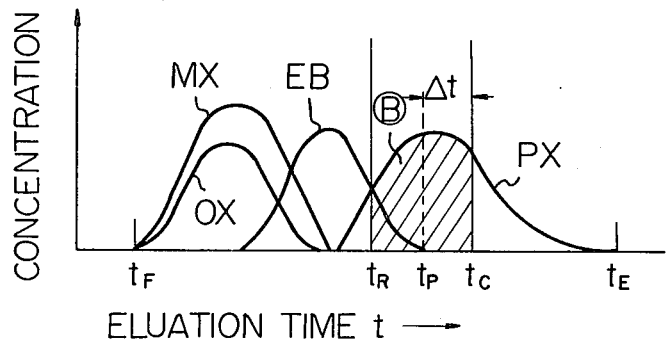

Chromatographic separation was carried out in the same manner as described in Example 1 except that the starting mixture A was previously mixed with 3 g of PX prior to the charge and development thereof. The chromatogram thus obtained was shown in FIG. 8a.

From the chromatogram shown in FIG. 8a, a time $t_C$ for which the same amount of the intended component as in Example 1 was recovered was found to be 38 min. A time $t_R$ at which the concentration of the remaining intended component was zero was determined from the chromatogram. Thus, 11.3 cc of a portion B containing 27% of EB and 73% of PX was separately obtained.

Then, the portion B obtained above was mixed with 50 cc of a fresh starting mixture A and the desorbent, and the mixture was charged to the column in the same manner as mentioned above, whereby the mixture was developed. The above-defined times $t_C$ and $t_R$ were redetermined from the chromatogram thus obtained. Thereafter, the same operations were repeated, while the recovery amount of the intended component and the amount of the portion B in each operation were kept constant. Thus, a chromatogram shown in FIG. 8b was obtained. The recovery yields and the purity of the intended component were changed as shown in Table 1 below.

The following results were obtained at a steady state.
$t_C = 39.2$ min
$t_R = 34.5$ min
$t_P$(Time at position of purity limit $=99.5\%) = 37.5$ min
$t_F$ (Time at front end position) $=25.0$ min
$t_E$ (Time at rear end position) $=45.0$ min
$W_T$ (Band width) $=20$ min
Recovery amount of intended component $=1.5$ g Thus, an allowance time for cutting the desired component having a desired purity was 1.7 min. The purity of the intended component when it was recovered in the same amount as in Example 1 was 100% and the separation of the desired PX could be stably carried out as compared with Example 1 since the allowance time for cutting the intended component having a purity limit.

Example 3

Chromatographic separation was carried out in the same manner as described in Example 2 except that the portion B obtained at the initial development was not mixed with the fresh mixture A but charged to the column subsequent to the starting mixture A.

The above-defined times $t_C$ and $t_R$ were determined from the chromatogram thus obtained. Thereafter, the same operations were repeated, while the recovery amount of the intended component and the amount of the portion B in each operation were kept constant. The recovery yields and the purity of the intended component were changed as shown in Table 1 below.

The following results were obtained at a steady state.
$t_C = 38.8$ min
$t_R = 34.0$ min
$t_P = 36.4$ min
$t_F = 25.5$ min
$t_E = 44.0$ min
$W_T = 18.5$ min
Recovery amount of intended component = 1.5 g Thus, an allowance time for cutting the intended component having a desired purity was 2.4 min. It is clear from the results shown above that the allowance time was further increased as compared with Example 2 by charging the portion B not together with the mixture A but subsequent to the mixture A.

Example 4

Figure 9:
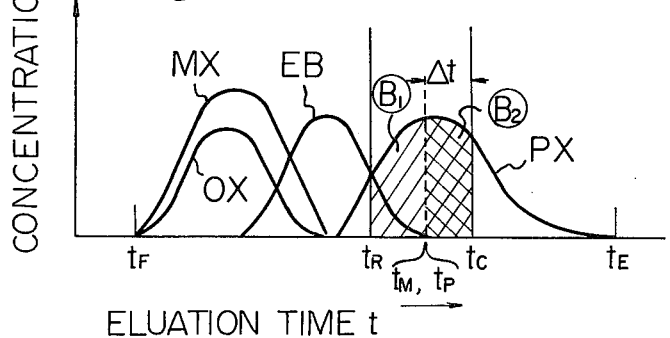

This example was based on the chromatogram after the steady state was obtained. The chromatogram is shown in FIG. 9.

The specific points of the chromatogram were as follows.

$t_C$ (Time at which the same amount of the intended component as in Example 1 was recovered) = 38.8 min $t_P$ (Time at position at which the intended component having a purity limit of 99.5% is obtained) = 36.4 min $\Delta t$ (Time difference between allowance times for cutting the intended component of this Example and Example 1) = 2.4 min $t_F$ (Time at front end position) = 25.5 min $t_E$ (Time at rear end position) = 44.0 min From the chromatogram obtained above, the time at which the portion B should be recharged in the next operation was determined.

$t_R$ (Time before which the concentration of the remaining intended component was zero, in front of $t_C$) = 34.0 min $t_M$ (Time after which the purity of the intended component was the desired purity or more, in the portion B between $t_C$ and $t_R$) = 36.4 min Thus, 5.2 cc of portion $B_1$ (between $t_R$ and $t_M$) containing 37.7% of EB, 62.3% of PX, and 6.1 cc of portion $B_2$ (between $t_M$ and $t_C$) containing 0.6% of EB and 99.4% of PX, in this elution order, were separately obtained.

Then, the portions $B_1$ and $B_2$ obtained above, 50 cc of the fresh starting mixture A and the desorbent were charged to the column in the order of the mixture A and the portions $B_1$ and $B_2$ and, then, developed with the desorbent.

The above-defined times $t_C$ and $t_M$ were redetermined from the chromatogram thus obtained. Thereafter, the same operations were repeated, while the recovery amount of the intended component and the amounts of the portions $B_1$ and $B_2$ in each operation were kept constant. The recovery yields and the purity of the intended component were changed as shown in Table 1 below.

The following results were obtained at a steady state.
$t_C = 38.7$ min
$t_M = 34.4$ min
$t_R = 32.4$ min
$t_P = 34.4$ min
$t_F = 25.7$ min
$t_E = 44.1$ min
$W_T = 18.4$ min
Recovery amount of intended component = 1.5 g Thus, an allowance time for cutting the intended component having a desired purity was 4.3 min. As is clear from the results shown above, the allowance time $\Delta t$ was further increased as compared with Example 3 by recharging the portion B after dividing it into two portions $B_1$ and $B_2$ in the elution order.

Example 5

Chromatographic separation was carried out in the same manner as described in Example 3 except that the desorbent was charged in such a manner that the front end of MX at the next band overlapped with the rear tailing portion of PX by shortening the charge time of the desorbent.

The specific points of the chromatogram were as follows.
$t_C = 38.2$ min
$t_P = 36.4$ min
$\Delta t = 1.8$ min
$t_F = 25.5$ min
$t_E$ (Time at front end position of next band) = 41.5 min The front end of the next band was overlapped to the rear end position at $t_E$, of the intended component of the first band due to the charge amount of the desorbent was decreased. As a result, the position of $t_C$ was somewhat deviated to the front side. The allowance time was still 1.8 min although $\Delta t$ was shortened.

From the chromatogram obtained above, the time at which the portion B should be recharged at the next operation was determined.

$t_R = 34.0$ min

Thus, 10.5 cc of portion B (between $t_C$ and $t_R$) containing 82% of PX and 18% of EB was separately obtained.

Then, the portion B obtained above, 50 cc of the fresh starting mixture A and the desorbent were charged to the column in the order of the mixture A and the portion B and, then, developed with the desorbent.

The above-defined time $t_C$ was redetermined from the chromatogram thus obtained. Thereafter, the same operations were repeated, while the recovery amount of the intended component and the amount of the portion B in each operation were kept constant. The recovery yields and the purity of the intended component were changed as shown in Table 1 below. The recovery yield was somewhat decreased by the tailing portion of PX overlapped by the next band but it was only about 1%.

The following results were obtained at a steady state.
$t_C = 38.1$ min
$t_R = 34.0$ min $t_P = 36.2$ min
$t_F = 25.5$ min
$t_E = 41.5$ min
$W_T = 16.0$ min
Recovery amount of intended component = 1.5 g Thus, an allowance time Δt for cutting the intended component having the desired purity was 1.9 min. The allowance time Δt was decreased by overlapping the rear end of PX with the front end of the next MX band. However, the amount of the desorbent used was decreased to 0.79 times as compared with Example 3, since the band width of one cycle was decreased and the portion where the concentration of the desorbent used was high could be omitted by the overlapping.

Example 6

Figure 11:
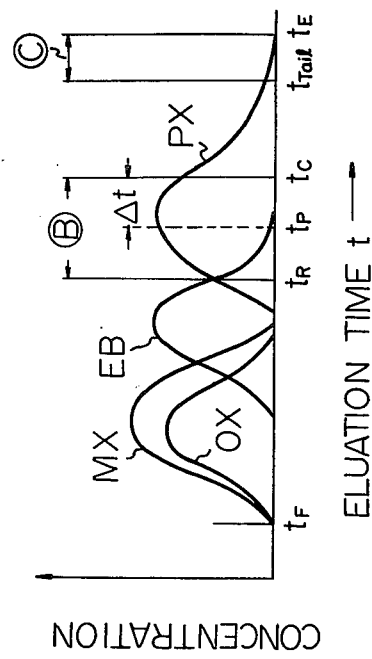

Chromatographic separation was started from the chromatogram of Example 3 after reaching at a steady state. The chromatogram thus obtained is shown in FIG. 11.

The specific points of the chromatogram are as follows.

$t_C = 38.1$ min
$t_P = 36.4$ min
$\Delta t = 1.7$ min
$t_F = 25.5$ min
$t_E = 44$ min From the chromatogram obtained above, the time at which the portion B should be recharged at the next cycle was determined.

$t_R = 34.0$ min

Thus, 10.2 cc of portion B (between $t_C$ and $t_R$) containing 82% of PX and 18% of EB was separately obtained. The tailing portion of the intended component was cut at a position of $t_{Tail} = 41$ min and a portion between $t_{Tail}$ and $t_E$ was separately obtained as portion C without using the elutant.

Then, the portions B and C obtained above and 50 cc of the fresh starting mixture A and the desorbent were charged to the column in the order of portion C, mixture A, portion B and the desorbent.

The above-defined $t_C$ was redetermined from the chromatogram thus obtained. The time $t_{Tail}$ was determined in each repeated cycle such that the concentration of the intended component is the same as that of the previous cycle. Thereafter, the same operations were repeated, while the amount of the recovered intended component and the amounts of portions B and C in each operation were kept constant. The recovery yield and the purity of the intended component in each operation were changed as shown in Table 1 below.

The following results were obtained at a steady state.

$t_C = 38.1$ min
$t_R = 34.0$ min
$t_{TAil} = 41$ min
$t_P = 36.4$ min
$t_F = 25.5$ min
$t_E = 44$ min
$W_T = 18.5$ min
Recovery amount of intended component = 1.5 g Thus, an allowance time for cutting the intended component having a desired purity was 1.7 min.

The amount of the desorbent used was decreased to 0.75 times as compared with Example 3 since PX tailing portion C having a high desorbent concentration was directly recharged to the column without separating the desorbent.

Example 7 (Comparative)

Six stainless steel cylindrical columns gathering collectors at the top and bottom thereof, and each provided with a jacket and liquid distributors and liquid each having an inner diameter of 8 mm and a length of 2.5 m were connected in series with stainless steel pipes each having an inner diameter of 1 mm to provide a chromatographic separation column. The columns were packed with a potassium ion exchanged Y type zeolite having a particle size of 50 to 150 meshes. The columns were stabilized at a temperature of 55° C. and, then, a desorbent, isopropyl ether was charged to the columns to condition the packing in the columns. Then, 83.7 cc (corresponding to 0.19 cc/unit weight of the packing) of a starting mixture A (a so-called mixed xylene) to be separated in this column containing 21.5% of PX, 10.9% of EB, 45.1% of MX and 22.5% of OX was downwardly charged to the column by a constant rate pump. Thus, a adsorption band was formed. Subsequently, the desorbent was downwardly charged to the column at a flow rate of 8.37 cc/min, thereby developing the above-mentioned adsorption band. Eluates discharged from the bottom of the column were collected as fractions at intervals of 30 seconds. Each fraction was quantitatively determined by a gas chromatograph to obtain weight concentrations of the starting components and the desorbent in each sample.

Figure 12:
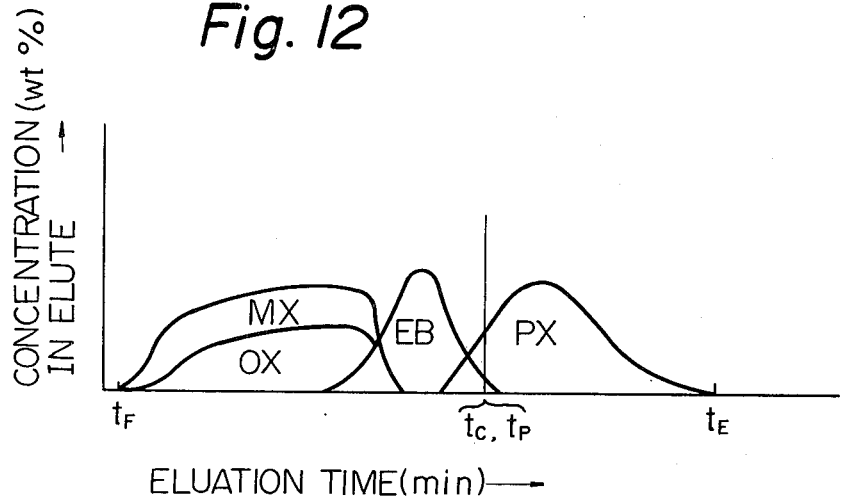

The results are shown in a chromatogram of FIG. 12 in which the abscissa axis represents a time from the initiation of the charge and the development and the ordinate axis represents the concentration of each adsorbed component. From the results of the chromatogram, it was found that the purity of the desired component PX was 99.5% and the elution time $t_P$ thereof was 81.6 min.

The time at $t_P$ was fixed and the separation operations were repeated. The recovery yields of the intended component in the starting mixture A and the purities of the recovered intended component were changed as shown in Table 1 below. The average recovery amount of the intended component was 13.9 g.

At the steady state in FIG. 12, $t_F$, $t_E$ and $W_T$ were 57.0 min, 101 min and 44.0 min, respectively. The amount of the desorbent required to recover the unit amount of the intended component was 14.8 g/g and the so-called area-time yield (hereinafter referred to as "ATY") which is defined as the amount of the intended component per the unit cross-sectional area of the column and unit time and which represents an availability efficiency of the column was 0.63 g/min·cm$^2$.

Example 8

Figure 13:
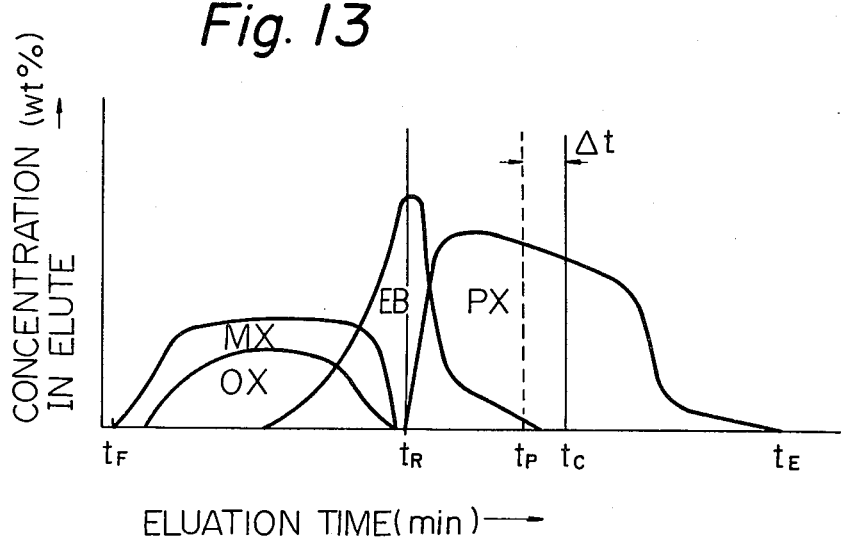

Chromatographic separation was carried out in the same manner as described in Example 7 except that the starting mixture A was previously mixed with an addition portion B containing 72.9% of PX and 27.1% of EB prior to the charge thereof to the column. The chromatogram thus obtained is shown in FIG. 13.

The specific points of the chromatogram were as follows.

$t_C$*hu 1 = 89.2 min.
$t_P = 85.8$ min
$\Delta t = 3.4$ min
$t_F = 59.0$ min
$t_E = 104.5$ min

*1 Time at which the total integrated amount of the intended component from the rear end of the intended component equals to the amount of the intended component in the mixture A.

From the chromatogram obtained above, the time at which the portion B should be recharged at the next operation was determined.

$t_R*2 = 78.0$ min

*2 Time at which the total amount of each component from the front end of the chromatogram equals to the total amount of the components other than the intended component in the mixture A.

Thus, 56.5 cc of portion B (between $t_C$ and $t_R$) containing 72.9% of PX and 27.1% of EB was separately obtained.

Then, the portion B obtained above was mixed with 83.7 cc of the fresh starting mixture A and the desorbent and, then, the mixture was charged and developed in the same manner as mentioned above.

The above-defined times $t_C$ and $t_R$ were redetermined from the chromatogram thus obtained. Thereafter, the same operations were repeated, while $t_C$ and $t_R$ were kept constant. The recovery yield and the purity of the intended component were changed as shown in Table 1 below.

The following results were obtained at a steady state.
$t_P = 85.8$ min
$t_F = 59.0$ min
$t_E = 104.5$ min
$W_T = 45.5$ min
Recovery amount of intended component = 15.5 g
$\Delta t = 3.4$ min
S*32 11.2
ATY = 0.68 g/min·cm$^2$

* The amount of the desorbent used per the unit amount of the intended component recovered (weight ratio).

Thus, according to the present invention, the desired component having a purity of 100% was surprisingly recovered at a recovery efficiency of 100% since the chromatographic separation was carried out after increasing the concentration of the intended component in the starting mixture A. This is a really unexpected effect as compared with the conventional method. The allowance time for keeping the 99.5% purity of the intended component was extended to as high as 3.4 min. Furthermore, the amount of the desorbent to be used was decreased due to the increase in the concentration of the adsorbate and, also, the available efficiency of the column was increased since the band width was narrowed although the recovery amount of the intended component PX was increased.

Example 9

Chromatographic separation was carried out in the same manner as described in Example 8 except that two stainless steel cylindrical columns each having an inner diameter of 8 mm and a length of 2.5 m were further connected to the separation column with stainless steel pipes each having an inner diameter of 1 mm and packed with the same zeolite as in Example 8 to provide a separation column having a total length of 20 m and also that the charge amount of the starting mixture A to the column was changed to 98.3 cc (corresponding to 0.17 cc/unit weight of the packing).

The chromatogram thus obtained is shown in FIG. 14a.

$t_C = 117.1$ min (see Example 8)
$t_P = 111.1$ min
$\Delta t = 6.0$ min
$t_F = 78$ min
$t_E = 134$ min From the chromatogram obtained above, the time at which the portion B should be recharged at the next operation was determined.

$t_R = 103.3$ min (see Example 8)

Thus, 64.5 cc of portion B (between $t_C$ and $t_R$) containing 72.9% of PX and 27.1% of EB was separately obtained.

Then, the portion B obtained above was mixed with 98.3 cc of the fresh starting mixture A and the desorbent and, then, the mixture was charged and developed in the same manner as mentioned above.

The above-defined times $t_C$ and $t_R$ were redetermined from the chromatogram thus obtained. Thereafter, the same operations were repeated, while $t_C$ and $t_R$ were kept constant. The recovery yield and the purity of the intended component were changed as shown in Table 1 below.

The following results were obtained at a steady state.
$t_P = 111.1$ min
$t_F = 78$ min
$t_E = 134$ min
$W_T = 56$ min
Recovery amount of intended component = 18.2 g
$\Delta t = 6.0$ min
S = 12.1
ATY = 0.65 g/min·cm$^2$ As is clear from the results shown above, the allowance time for keeping the desired purity was further extended as compared with Example 8. Although the amount of the desorbent used and the available efficiency of the column were somewhat inferior to those in Example 8 due to the fact that the developing time was extended, this approach is very effective in the case where the cutting accuracy cannot be increased as required.

Example 10

Chromatographic separation was carried out in the same manner as described in Example 9 except that the addition portion B was not mixed with the starting mixture A but charged subsequent to the mixture A and, then, the desorbent was charged, thereby effecting the development.

The chromatogram thus obtained is shown in FIG. 14b.

This specific points of the chromatogram were as follows.

$t_C = 117.2$ min (see Example 8)
$t_P = 111.2$ min
$\Delta t = 6.0$ min
$t_F = 78$ min
$t_E = 134$ min From the chromatogram obtained above, the time at which the portion B should be recharged at the next operation was determined.

$t_R = 102.9$ min (see Example 8)

Thus, 64.5 cc of portion B (between $t_C$ and $t_R$) containing 72.9% of PX and 27.1% of EB was separately obtained.

A time $t_Q$ which was the rear end position of MX and OX was 100.3 and, therefore, there was an allowance time of 2.6 min between $t_R$ and $t_Q$. This means that the amount of the starting mixture A to be charged can be increased. Therefore, the amount of the starting mixture A charged in the subsequent repeated operation was increased to 134 cc (corresponding to 0.23 cc/g of the packing).

Then, the portion B obtained above, 134 cc of the starting mixture A and the desorbent were subsequently charged to the column in the order of A and B, and developed with the desorbent.

The above-defined times $t_C$ and $t_R$ were redetermined from the chromatogram thus obtained. Thereafter, the same operations were repeated, while $t_C$ and $t_R$ were kept constant. Thus, the chromatogram shown in FIG. 14b was obtained and the recovery yield and the purity of the intended component were changed as shown in Table 1 below.

The following results were obtained at a steady state.
$t_P = 114.1$ min
$t_F = 78$ min
$t_E = 136.5$ min
$W_T = 58.5$ min
Recovery amount of intended component = 24.8 g
$\Delta t = 3.0$ min
$S = 8.5$
$ATY = 0.84$ g/min cm$^2$ The allowance time was decreased as compared with Example 9 since the amount of the charged starting mixture A was increased. However, the amount of the desorbent used was remarkably decreased and the availability efficiency of the column was remarkably improved. Thus, this technique provides economical separation when a suitable cutting accuracy can be ensured. That is to say, the results of Examples 9 and 10 clearly show that these techniques can be fairly flexibly applied in the desired separation required by users. Furthermore, the recharge of the separated portion B subsequent to the starting mixture A without mixing thereof with the mixture A will contribute to the good separation since wasteful mixing of the separated portion B again with the mixture A is not carried out.

Example 11

Chromatographic separation was carried out in the same manner as described in Example 10 except that the following variation was made.

Figure 10:
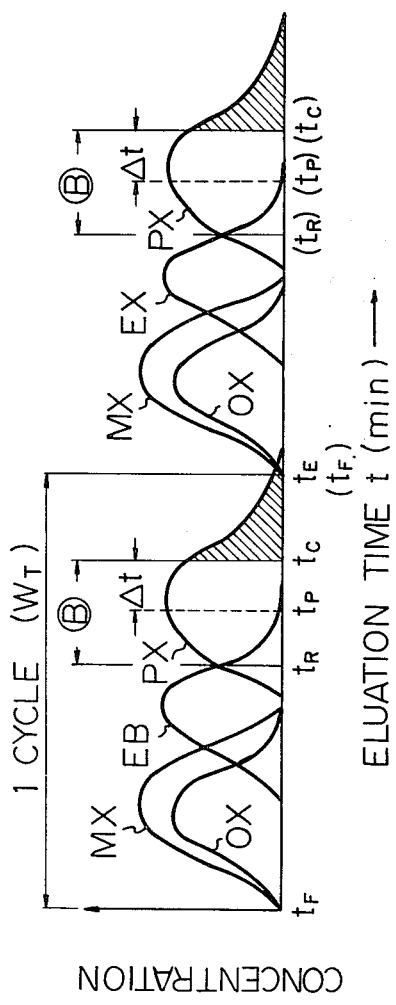

That is, a portion B corresponding to that between $t_R$ and $t_C$ in the steady state chromatogram was divided into two portions at a position $t_M$ 111.3 min where the purity of PX in the portion B between $t_R$ and $t_C$ became 99.5%. The portion B, between $t_R$ and $t_M$ and the portion B$_2$ between $t_M$ and $t_C$ were charged to the column, after removing the desorbent therefrom, subsequent to the starting mixture A in the order of A, B$_1$ and B$_2$ and, then, developed with the desorbent. The chromatogram thus obtained is shown in FIG. 10.

The specific points of the chromatogram were as follows.
$t_C = 116.3$ min (see Example 8)
$t_P = 110.1$ min
$\Delta t = 6.2$ min
$t_F = 78.0$ min
$t_E = 136.5$ min From the chromatogram obtained above, the time at which the portion B should be recharged at the next operation was determined.
$t_R = 105$ min (see Example 8)
$t_M = 108$ min Thus, 36.3 cc of portion B$_1$ containing 56.6% of PX and 47.4% of EB, and 28.2 cc of portion B$_2$ containing 99.0% of PX and 1.0% of EB were separately obtained in this order.

Then, the portions B$_1$ and B$_2$ obtained above, and 134 cc of the fresh starting mixture A were charged and, then, developed with the desorbent, in the same manner as mentioned above.

The above-defined times $t_C$, $t_R$, and $t_M$ were redetermined from the chromatogram thus obtained. Thereafter, the same operations were repeated, while $t_C$, $t_R$, and $t_M$ were kept constant. The recovery yield and the purity of the intended component were changed as shown in Table 1 below.

The following results were obtained at a steady state.
$t_P = 108.8$ min
$t_F = 78.0$ min
$t_E = 136.5$ min
$W_T = 58.5$ min
Recovery amount of intended component = 24.8 g
$\Delta t = 7.5$ min
$S = 8.5$
$ATY = 0.84$ g/min·cm$^2$ As is clear from the above results, the separation efficiency was improved and the allowance time was increased to 7.5 min, as compared with Example 10, by dividing the portion B into two portions B$_1$ and B$_2$ and charging them, subsequent to the mixture A, to the column in the elution order.

Example 12

Figure 16:
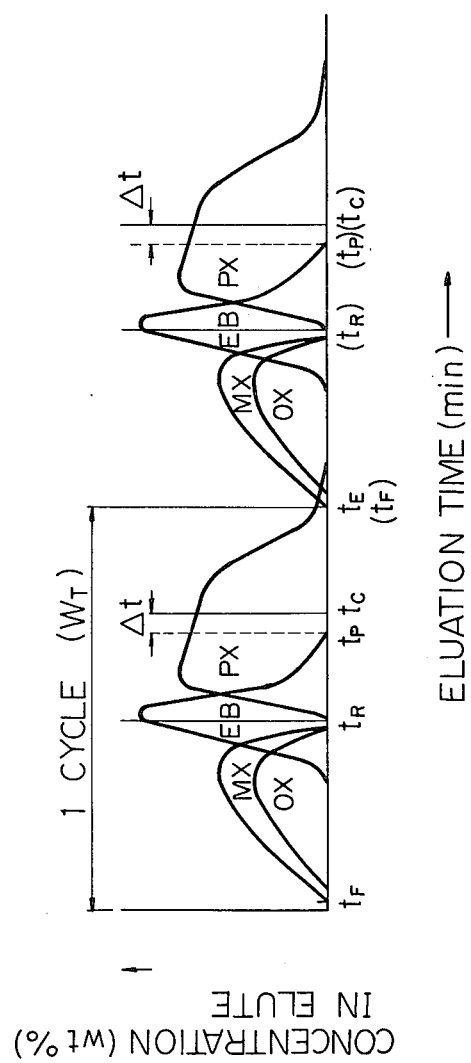

Chromatographic separation was carried out in the same manner as described in Example 10 except that, in the steady state condition of Example 10, the desorbent was charged at 28.8 min and, then, the next adsorption band was formed in such a manner that the tailing portion of the rear end of PX in the previous band is overlapped with the front end of MX in the subsequent band. The chromatogram thus obtained is shown in FIG. 16.

The specific points of the chromatogram were as follows.
$t_C = 117.5$ min (see Example 8)
$t_P = 114.5$ min
$\Delta t = 3.0$ min
$t_F = 78.0$ min
$t_E = 130.5$ min (see Example 8)

From the chromatogram obtained above, the time at which the portion B should be recharged at the next operation was determined.
$t_R = 105.0$ min (see Example 8)

Thus, 64.5 cc of the portion B (between $t_C$ and $t_R$) containing 72.9% of PX and 27.1% of EB was separately obtained.

Then, the portion B obtained above, and 134 cc of the fresh starting mixture A were charged and developed with the desorbent, in the same manner as mentioned above.

The above-defined times $t_C$ and $t_R$ were redetermined from the chromatogram thus obtained. Thereafter, the same operations were repeated, while $t_C$ and $t_R$ were kept constant. The recovery yield and the purity of the intended component were changed as shown in Table 1 below.

The following results were obtained at a steady state.
$t_P = 114.5$ min
$t_F = 78.0$ min
$t_E = 130.5$ min
$W_T = 52.5$ min
Recovery amount of intended component = 24.1 g
$\Delta t = 3.0$ min
$S = 7.2$
$ATY = 0.91$ g/min·cm$^2$ As is clear from the above results, the column availability efficiency was remarkably increased due to the decrease in the band width and the amount of the desorbent used was remarkably decreased due to the decrease in the amount of the portion containing a high concentration of the desorbent. The recovery yield of PX was decreased by the amount corresponding to the portion of the PX overlapped with the front end of the next band. However, this decrease was not large.

Example 13 (Comparative)

Six stainless steel cylindrical columns each provided with a jacket and liquid distributors and liquid gathering collectors at the top and bottom thereof and each having an inner diameter of 20 mm and a length of 2.5 m were connected in series with stainless steel pipes each having an inner diameter of 8 mm to provide a chromatographic separation column. The columns were packed with the same zeolite as used in Example 7. The column was stabilized at a temperature of 55° C. and, then, the same desorbent as used in Example 7 was charged to the column to condition the packing in the column. Then, 523 cc (corresponding to 0.19 cc/unit weight of the packing) of the same mixture A as used in Example 7 was downwardly charged to the column by a constant rate pump. Thus, an adsorption band was formed. Subsequently, the desorbent was downwardly charged to the column at a flow rate of 52.3 cc/min, thereby developing the above-mentioned adsorption band. Eluates discharged from the bottom of the column were collected as fractions at intervals of 30 seconds. Each fraction was quantitatively determined by a gas chromatography to obtain the weight concentrations of the starting components and the desorbent in each sample.

The results are as shown in the chromatogram of FIG. 12 in which the abscissa axis represents the time of the initiation of the charge and the development and the orginate axis represents the concentration of each adsorbed component. From the results of the chromatogram, it was found that the purity of the desired component PX was 99.5% and the eluation time $t_P$ thereof was 82.7 min.

The time at $t_P$ was fixed and the separation operations were repeated. The recovery yields of the intended component in the starting mixture A and the purities of the recovered intended component were changed as shown in Table 1 below. The average recovery amount of the intended component was 76.5 g.

At the steady state in FIG. 12, $t_F$, $t_E$ and $W_T$ were 56.5 min, 101.0 min and 44.5 min, respectively. The amount of the desorbent required to recover the unit amount of the desired component was 16.5 g/g, and ATY was 0.55 g/min·cm².

As is clear from the above results, the increase in the column diameter to 20 mm results in the flattening of the chromatogram, the remarkable decrease in the recovery yield of PX, and also the remarkable decreases in the amount of the desorbent used and the column availability efficiency, as compared with Example 7.

Example 14

The chromatographic separation was carried out in the same manner as described in Example 13 except that two stainless steel cylindrical columns each having an inner diameter of 20 mm and a length of 2.5 m were further connected, in series, to the separation column with stainless steel pipes each having an inner diameter of 8 mm and which columns were packed with the same zeolite as in Example 13 to provide a separation column having a total length of 20 m and except that 838 cc (corresponding to 0.23 cc/unit weight of the filler) of the starting mixture A was charged to the column and, then, 403 cc of the portion B having the same composition as that of Example 9 was charged to the column.

Figure 14:
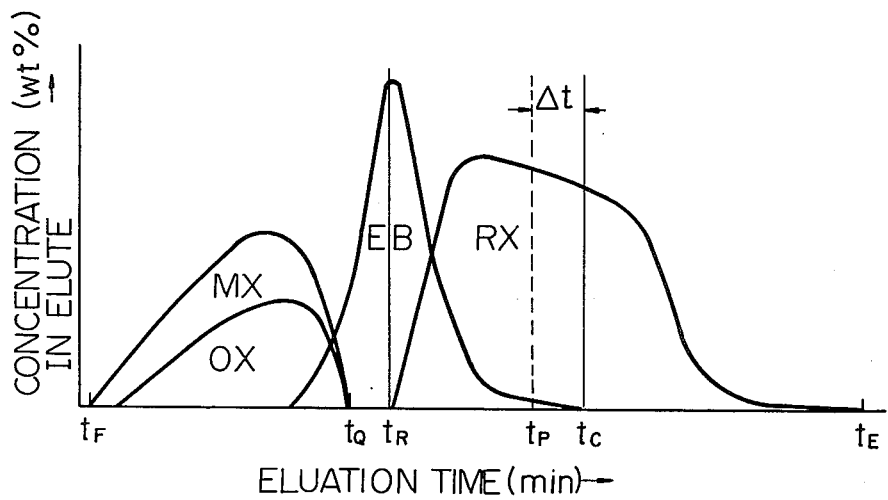
Figure 14:
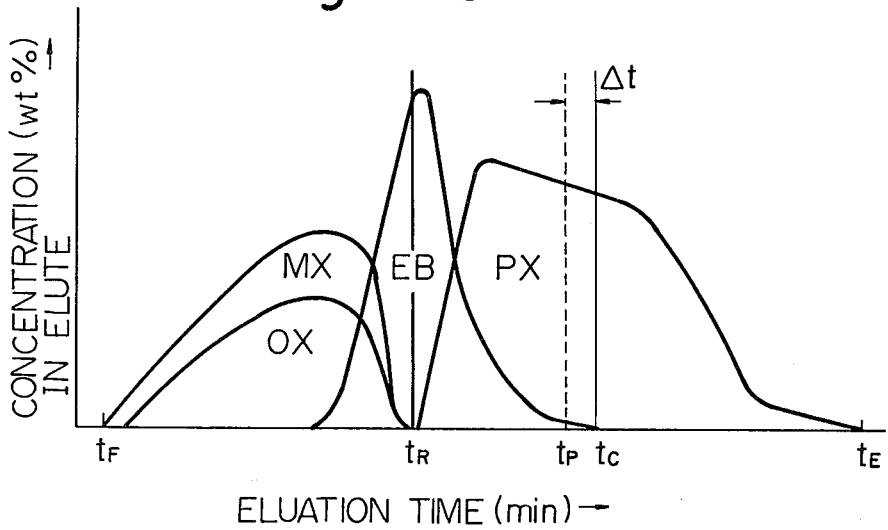

The chromatogram thus obtained is shown in FIG. 14. The results are as follows.

$t_C = 117.2$ min (see Example 8)
$t_P = 115.8$ min
$\Delta t = 1.4$ min
$t_F = 78.0$ min
$t_E = 137.5$ min From the chromatogram obtained above, the time at which the portion B should be recharged at the next operation was determined.

$t_R = 104.7$ min (see Example 8)

Thus, 403 cc of portion B (between $t_C$ and $t_R$) containing 66.7% of PX and 33.3% of EB was separately obtained.

Then, the portion B obtained above, 838 cc of the fresh starting mixture A and the desorbent were charged and developed in the same manner as mentioned above.

The above-defined times $t_C$ and $t_R$ were redetermined from the chromatogram thus obtained. Thereafter, the same operations were repeated, while $t_C$ and $t_R$ were kept constant. The recovery yield and the purity of the intended component were changed as shown in Table 1 below.

The following results were obtained at a steady state.
$t_P = 114.3$ min
$t_F = 57.5$ min
$t_E = 138.0$ min
$W_T = 60.5$ min
Recovery amount of desired component = 155 g
$\Delta t = 2.9$ min
$S = 9.8$
ATY = 0.82 g/min·cm²

As is clear from the above results, the remarkable worsening in conventional Example 13 caused by the scale-up of the column diameter to 20 mm was satisfactorily eliminated by the present invention. Thus, the intended component having a purity of 100% was separately recovered at a recovery efficiency of 100% with a sufficient allowance time. Furthermore, the amount of the desorbent used and the column availability efficiency were improved substantially as the same as in the case of the column having a diameter of 8 mm.

Example 15 (Comparative)

Six stainless steel cylindrical columns gathering collectors at the top and bottom thereof, and each provided with a jacket and liquid distributors and liquid each having an inner diameter of 200 mm and a length of 2.5 m were connected in series with stainless steel pipes each having an inner diameter of 15 mm to provide a chromatographic separation column. The column was packed with the same zeolite as used in Example 7. The column was stabilized at a temperature of 55° C. and, then, the same desorbent as used in Example 7 was charged to the column to condition the filler in the column. Then, 52.3 1 (corresponding to 0.19 cc/unit weight of the filler) of the starting mixture A having the same composition as used in Example 7 was downwardly charged to the column by a constant rate pump.

Thus, an adsorption band was formed. Subsequently, the desorbent was downwardly charged to the column at a flow rate of 5.23 l/min, thereby developing the above-mentioned adsorption band. Eluates discharged from the bottom of the column were collected as fractions at intervals of 30 seconds. Each fraction was quantitatively determined by a gas chromatography to obtain weight concentrations of the starting components and the desorbent in each sample.

The results are as shown in a chromatogram of FIG. 12 in which the abscissa axis represents a time from the initiation of the charge and the development and the ordinate axis represents the concentration of each adsorbed component. From the results of the chromatogram, it was found that the purity of the intended component PX was 99.5% and the elution time $t_P$ thereof was 84.8 min.

The time at $t_P$ was fixed and the separation operations were repeated. The recovery yields of the intended component in the starting mixture A and the purities of the recovered intended component were changed as shown in Table 1 below. The average recovery amount of the intended component was 6.0 kg.

At the steady state in FIG. 12, $t_F$, $t_E$ and $W_T$ were 56.5 min, 99.5 min and 43.0 min, respectively. The amount of the desorbent required to recovers the unit amount of the intended component was 20.7 g/g, and ATY was 0.44 g/min·cm$^2$.

As is clear from the above results, the further scale-up of the column diameter to 200 mm results in the further remarkable decrease in the recovery yield of the desired component, and both the amount of the desorbent used and the column availability efficiency became worse to such an extent that this technique is substantially impossible to practically used from an economical viewpoint.

Example 16

Chromatographic separation was carried out in the same manner as described in Example 15 except that two stainless steel cylindrical columns each having an inner diameter of 200 mm and a length of 2.5 m were further connected, in series, to the separation column and which columns were packed with the same zeolite as in Example 15 to provide a separation column having a total length of 20 m, and also that 83.8 liters (corresponding to 0.23 cc/g of the packing) of the starting mixture A, 23.2 liters of the portion B, having the same composition as that of the initial portion $B_1$ of Example 11, 17.1 liters of the portion $B_2$ having the same composition as that of the initial portion $B_2$ of Example 11 and the desorbent were charged to the column and developed.

Figure 15:
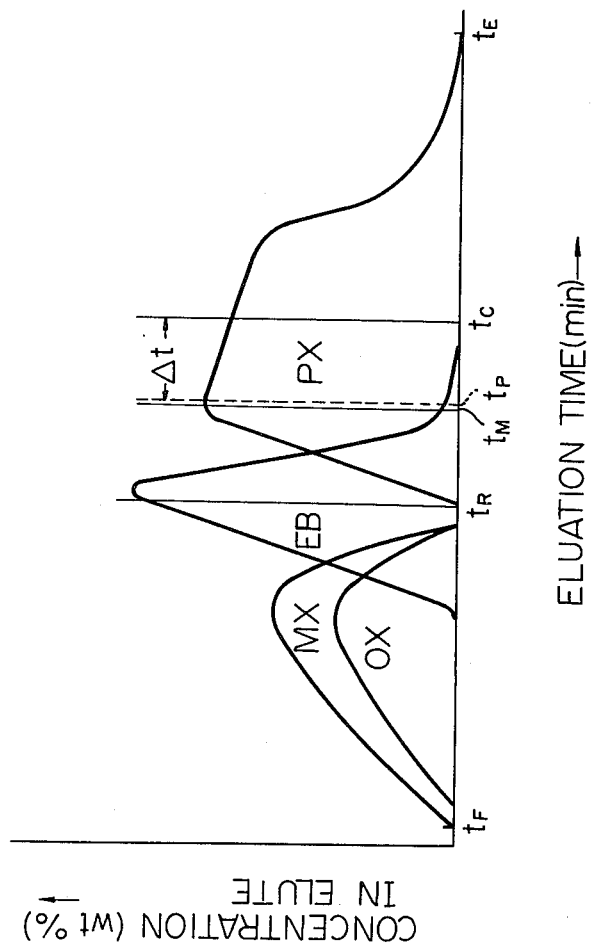

The chromatogram thus obtained is shown in FIG. 15.

$t_C = 117.2$ min (see Example 8)
$t_P = 113.4$ min
$\Delta t = 3.8$ min
$t_F = 77.6$ min
$t_E = 138.5$ min From the chromatogram obtained above, the time at which the portion B should be recharged at the next operation was determined.

$t_R = 103.9$ min (see Example 8)
$t_M = 110.0$ min (see Example 11)

Thus, 23.7 liters of portion $B_1$ (between $t_R$ and $t_M$) containing 44.8% of EB and 55.2% of PX and 16.6 liters of portion $B_2$ (between $t_M$ and $t_C$) containing 1.8% of EB and 98.2% of PX were separately obtained in this order.

Then, the portions $B_1$ and $B_2$ obtained above, 83.8 liters of the fresh starting mixture A, and the desorbent were charged and developed in the same manner as mentioned above.

The above-defined times $t_C$, $t_R$, and $t_M$ were redetermined from the chromatogram thus obtained. Thereafter, the same operations were repeated, while $t_C$, $t_R$ and $t_M$ were kept constant. The recovery yield and the purity of the intended component were changed as shown in Table 1 below.

The following results were obtained at a steady state.

$t_P = 113.1$ min
$t_F = 77.6$ min
$t_E = 138.5$ min
$W_T = 60.9$ min
Recovery amount of intended component = 15.5 kg
$\Delta t = 4.1$ min
$S^* = 9.0$
ATY = 0.81 g/min·cm$^2$ As is clear from the above results, the remarkable worsening in the conventional method of Example 15 caused by the scale-up of the column diameter to 200 mm was surprisingly eliminated by the present invention. Thus, the desired component having a purity of 100% was separately recovered at a recovery efficiency of 100% with a sufficient allowance time. Furthermore, the amount of the desorbent used and the column availability efficiency were improved substantially as the same as in the case of the column having a diameter of 8 mm.

Example 17

The chromatographic separation was carried out in the same manner as described in Example 16 except that the spearation was started from the steady state condition of the chromatogram in Example 16.

Figure 17:
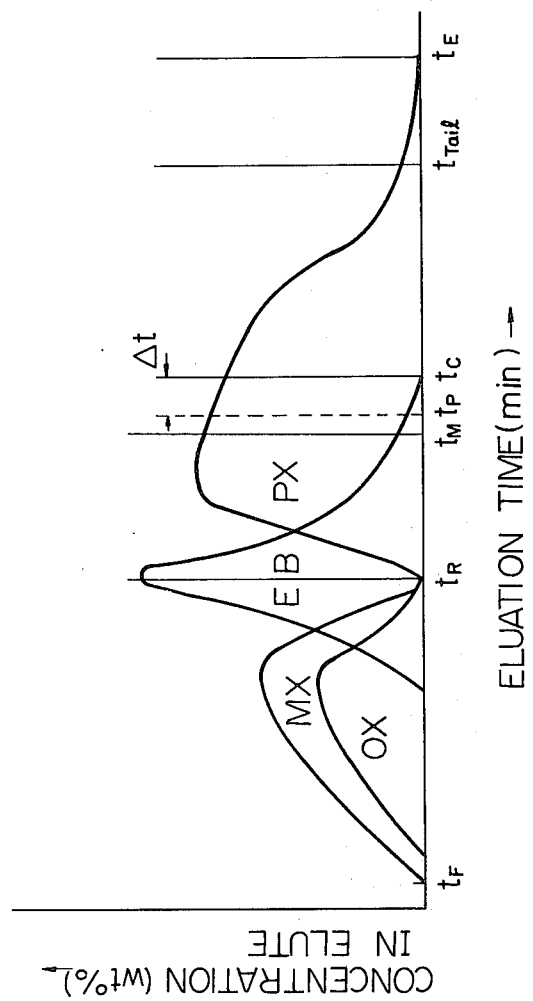

The chromatogram is shown in FIG. 17.

The specific points of the chromatogram were as follows.

$t_C = 117.0$ min (see Example 8)
$t_P = 113.4$ min
$\Delta t = 3.6$ min
$t_F = 77.6$ min
$t_E = 138.5$ min From the chromatogram obtained above, the time at which the portion B should be recharged at the next operation was determined as in Example 16.

$t_R = 103.9$ min (see Example 8)
$t_M = 110.0$ min (see Example 11)

Thus, 23.7 liters of portion $B_1$ (between $t_R$ and $t_M$) containing 44.8% of EB and 55.2% of PX and 16.3 liters of portion $B_2$ containing 1.8% of EB and 98.2% of PX were separately obtained in this order. The separation of the desired component was cut at the tailing portion thereof of $t_{Tail} = 135$ min and portion C (between $t_{Tail}$ and $t_E$) was separately obtained without removing the eluent.

Then, the portions $B_1$, $B_2$, and C, and 83.8 liters of the fresh starting mixture A were charged to the column in the order of C, A, B, and $B_2$ and developed with the desorbent. The $t_{Tail}$ was determined.

The above-defined times $t_C$, $t_R$, and $t_M$ were redetermined from the chromatogram thus obtained. Thereafter, the same operations were repeated, while $t_C$, $t_M$, and $t_{Tail}$ were kept constant. The recovery yield and the purity of the intended component were changed as shown in Table 1 below.

The following results were obtained at a steady state.
$t_P = 113.0$ min
$t_F = 77.6$ min
$t_E = 138.5$ min
$W_T = 60.9$ min
Recovery amount of intended component = 15.5 kg
$\Delta t = 4.0$ min
$S = 7.8$
$ATY = 0.81$ g/min·cm²

As is clear from the above results, when the PX tailing portion having a low adsorbate concentration was used as portion C without removing the desorbent therefrom by distillation or other separation techniques, the amount of the desorbent used was further decreased as compared with Example 16 so that the separation could be advantageously and economically carried out in a large column.

Example 18

Figure 18:
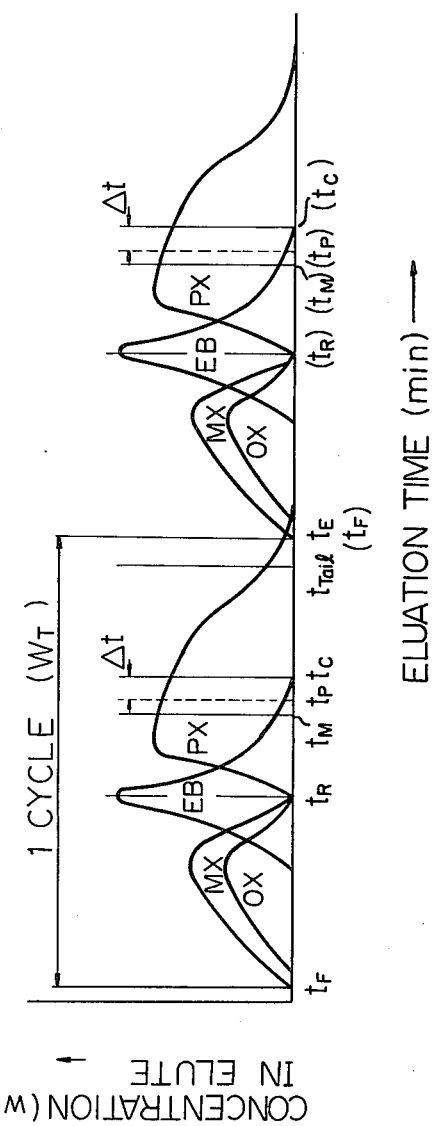

Chromatographic separation was carried out at the conditions after reaching the steady state of Example 17 in the same manner as described in Example 17 except that the desorbent was charged for 29.0 min in such a manner that the front end of MX at the next band was overlapped with the tailing portion of the rear end of MX at the previous band. The chromatogram thus obtained is shown in FIG. 18.

The specific points of the chromatogram were as follows.
$t_C = 117.0$ min (see Example 8)
$t_P = 113.4$ min
$\Delta t = 3.6$ min
$t_F = 77.6$ min
$t_E^* = 136.5$ min

* Time at front end position of next band.

The front end of the next band was overlapped with the rear end position at $t_E$ of the intended component of the previous band due to the charge amount of the desorbent was decreased.

From the chromatogram obtained above, the time at which the portion B should be recharged in the next operation was determined as in Example 17.
$t_R = 103.9$ min (see Example 8)
$t_M = 110.0$ min (see Example 11)

Thus, 23.7 liters of portion $B_1$ (between $t_R$ and $t_M$) containing 44.8% of EB and 55.2% of PX and 16.3 liters if portion $B_2$ (between $t_M$ and $t_C$) containing 1.8% of EB and 98.2% of PX were separately obtained in this order. The separation of the intended component was cut at the tailing portion thereof of $t_{Tail} = 135$ min and portion C (between $t_{Tail}$ and $t_E$) was separately obtained without removing the eluent.

Then, the portions $B_1$, $B_2$ and C, 83.8 liters of the fresh starting mixture A, and the desorbent were charged and developed in the same manner, as in Example 17.

The above-defined times $t_C$, $t_R$, and $t_M$ were redetermined from the chromatogram thus obtained. The $t_{Tail}$ was determined at a time such that the concentration of the intended component became the same as in the previous cycle. Thereafter, the same operations were repeated, while $t_C$, $t_R$, $t_M$, and $t_{Tail}$ were kept constant and the charge time of the desorbent between two adsorption band charges was kept 29 mim. The recovery yield and the purity of the intended component were changed as shown in Table 1 below.

The following results were obtained at a steady state.
$t_P = 113.0$ min
$t_F = 77.6$ min
$t_E = 138.5$ min
$W_T = 60.9$ min
Recovery amount of desired component = 15.46 kg
$\Delta t = 4.0$ min
$S = 7.8$
$ATY = 0.84$ g/min·cm²

As is clear from the above results, the overlapping with the next band results in the further increase in the column availability efficiency as compared with Example 17. Thus, according to the present invention, the desired separation can be carried out even by using a large column having a diameter as large as 200 mm in the same way as in the case of a column having a diameter of 8 mm. This example is the best mode of the present invention.

Example 19 (Comparative)

Six stainless steel cylindrical columns gathering collectors at the top and bottom thereof, and each provided with a jacket and liquid distributors and liquid each having an inner diameter of 8 mm and a length of 2.5 m were connected in series with stainless steel pipes each having an inner diameter of 1 mm to provide a chromatographic separation column. The columns were packed with the same zeolite as used in Example 7.

The columns were stabilized at a temperature of 75° C. and, then, a desorbent, n-propyl ether was charged to the columns to condition the packing in the columns. Then, 83.7 cc (corresponding to 0.19 cc/unit weight of the packing) of the starting mixture A having the same composition as in Example 7 was downwardly charged to the column to form a adsorption band.

Subsequently, the desorbent was downwardly charged to the column at a flow rate of 8.37 cc/min, thereby developing the above-mentioned adsorption band. Eluates discharged from the bottom of the column were collected as fractions at intervals of 30 seconds. Each fraction was quantitatively determined by a gas chromatography to obtain weight concentrations of the starting components and the desorbent in each sample.

The results are as shown in a chromatogram of FIG. 12 in which the abscissa axis represents the time of the initiation of the charge and the development and the ordinate axis represents the concentration of each adsorbed component. From the results of the chromatogram, it was found that the purity of the desired component PX was 99.5% and the elution time $t_P$ thereof was 79.8 min.

The time at $t_P$ was fixed and the separation operations were repeated. The recovery yields of the intended component in the starting mixture A and the purities of the recovered intended component were changed as shown in Table 1 below. The average recovery amount of the intended component was 12.7 g.

At the steady state in FIG. 12, $t_F$, $t_E$ and $W_T$ were 56.6 min, 98.7 min and 42.1 min, respectively. The amount of the desorbent required to recover the unit amount of the intended component was 15.2 g/g, and ATY was 0.60 g/min cm².

Example 20

The chromatographic separation was carried out by using the same apparatus and method as used in Example 10 except that the desorbent and the adsorption and separation temperature used in Example 10 were used. The chromatogram thus obtained is as shown in FIG. 14.

The specific points of the chromatogram were as follows.

$t_C = 115.1$ min (see Example 8)
$t_P = 110.6$ min
$\Delta t = 4.5$ min
$t_F = 77.5$ min
$t_E = 131$ min From the chromatogram obtained above, the time at which the portion B should be recharged in the next operation was determined.

$t_R = 78.0$ min (see Example 8)

Thus, 64.5 cc of portion B (between $t_C$ and $t_R$) containing 69.0% of PX and 31.0% of EB was separately obtained. The rear end position of MX and OX was at $t_Q = 99.6$ min and there was an allowance time of 2.2 min between $t_R$ and $t_Q$. This means that the charge amount of the starting mixture A could be increased. Accordingly, the amount of the starting mixture A charged in the subsequent repeated cycles was increased to 116.2 cc.

Then, the portion B obtained above, 116.2 cc of the fresh starting mixture A and the desorbent were charged and developed in the same manner as in Example 10.

The above-defined times $t_C$ and $t_R$ were redetermined from the chromatogram thus obtained. Thereafter, the same operations were repeated, while $t_C$ and $t_R$ were kept constant. The recovery yield and the purity of the intended component were changed as shown in Table 1 below.

The following results were obtained at a steady state.

$t_P = 114.1$ min
$t_F = 77.5$ min
$t_E = 132.3$ min
$W_T = 54.8$ min
Recovery amount of intended component = 21.5 g
$\Delta t = 1.2$ min
$S = 9.3$
$ATY = 0.78$ g/min·cm$^2$ It was observed that the desired similar results were obtained in the case where n-propyl ether was used as a desorbent in lieu of iso-propyl ether.

Example 21 (Comparative)

A stainless steel cylindrical column gathering collectors at the top and bottom thereof, and each provided with a jacket and liquid distributors and liquid each having an inner diameter of 8 mm and a length of 5 m was connected to each other with a stainless steel pipe having an inner diameter of 1 mm to provide a chromatographic separation column. The column was packed with a potassium ion exchanged X type zeolite. The column was stabilized at a temperature of 70° C. and, then, a desorbent, n-butyl ether was charged to the columns to condition the packing in the column. Then 16 g of a starting mixture A containing 37% of o-diethylbenzene (hereinafter referred to as "o-DEB"), 28% of m-diethylbenzene (hereinafter referred to as "m-DEB") and 35% of p-diethylbenzene (hereinafter referred to as "p-DEB") was downwardly charged to the column by a constant rate pump.

Thus, an adsorption band was formed. Subsequently, the desorbent was downwardly charged to the column at a flow rate of 8.4 cc/min, thereby developing the above-mentioned adsorption band. Eluates discharged from the bottom of the column were collected as fractions at intervals of 30 seconds. Each fraction was quantitatively determined by a gas chromatography to obtain weight concentrations of the starting components and the desorbent in each sample.

Figure 19:
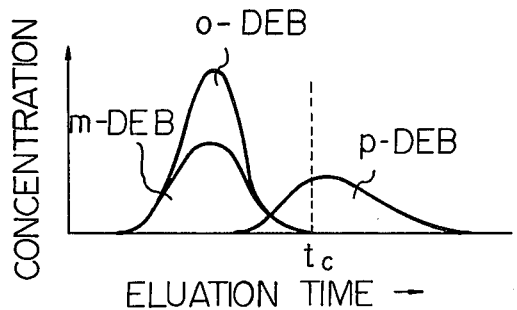

The results are as shown in a chromatogram of FIG. 19 in which the abscissa axis represents the time of the initiation of the charge and the development and the ordinate axis represents the concentration of each adsorbed component. From the results of the chromatogram, it was found that the purity of the intended component p-DEB was 99% and the elution time $t_P$ thereof was 21.9 min.

The time at $t_P$ was fixed and the separation operations were repeated. The recovery yields of the intended component in the starting mixture A and the purities of the recovered intended component were changed as shown in Table 1 below. The average recovery amount of the intended component was 2.8 g.

Example 22

Figure 20:
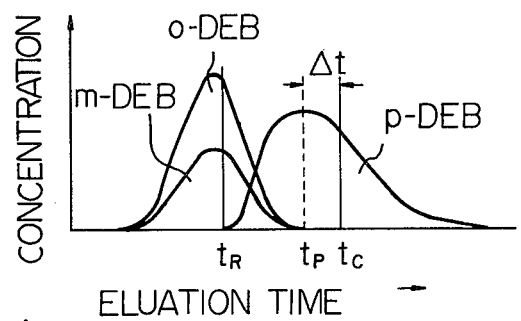
Figure 20:
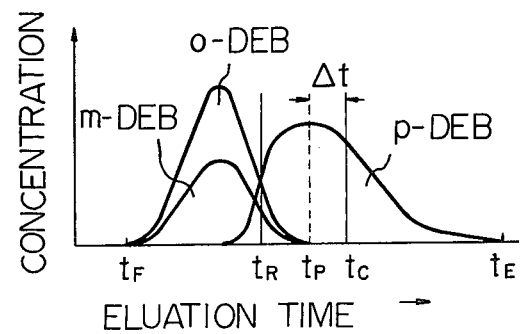

Chromatographic separation was carried out in the same manner as described in Example 21 except that the starting mixture A was previously mixed with 6.0 g of p-DEB prior to the charge and development thereof. The chromatogram thus obtained is shown in FIG. 20a.

Figure 21:
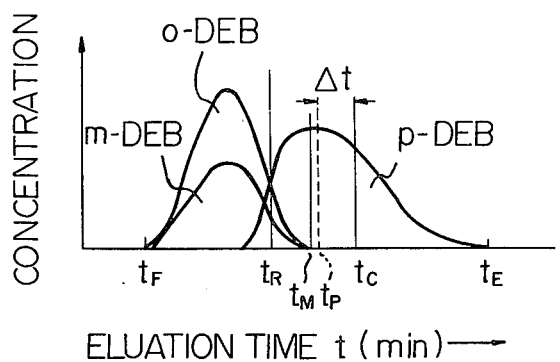

From the chromatogram shown in FIG. 21, a time $t_C$ for which the same amount of the recovered intended component as in Example 21 was obtained was found to be 23.2 min. A time $t_R$ before which the concentration of the remaining intended component was zero was determined from the chromatogram. Thus, 12.27 g of portion B (between $t_C$ and $t_R$) containing 28% of o-DEB, 21% of m-DEB, and 51% of p-DEB was separately obtained.

Then, the portion B obtained above, and 16 g of the fresh starting mixture A were charged to the column in the order of mixture A and portion B and developed with the desorbent.

The above-defined times $t_C$ and $t_R$ were redetemined from the chromatogram thus obtained. Thereafter, the same operations were repeated, while the recovery amount of the intended component and the amount of the portion B in each operation were kept constant. Thus, a chromatogram shown in FIG. 20 was obtained. The recovery yields and the purity of the intended component were changed as shown in Table 1 below.

The following results were obtained at a steady state.

$t_C = 24.8$ min
$t_R = 19.1$ min
$t_P$ (purity limit = 99%) = 21.8 min
$t_F = 14.0$ min
$t_E = 33.6$ min
$W_T = 19.6$ min
Recovery amount of intended component = 2.8 g Thus, an allowance time $\Delta t$ for cutting the intended component having a desired purity was 3.0 min.

Example 23

This example was based on the chromatogram of Example 22 after a steady state was obtained. The chromatogram is shown in FIG. 21.

The specific points of the chromatogram were as follows.

$t_C$ (Time at which the same amount of the intended component as in Example 21 was recovered) = 24.8 min $t_P$ (Time at position at which the intended component having a purity limit of 99% is obtained) = 21.8 min $\Delta t$ (Time difference between allowance times for cutting the intended component of this Example and Example 21) = 3.0 min $t_F$ (Time at front end position) = 14.0 min $t_E$ (Time at rear end position) = 33.6 min From the chromatogram obtained above, the time at which the portion B should be recharged in the next operation was determined.

$t_R$ (Time before which the concentration of the remaining intended component was zero, in front of $t_C$) = 19.1 min $t_M$ (Time after which the purity of the intended component was the desired purity or more, in the starting component B between $t_C$ and $t_R$) = 21.6 min Thus, 6.37 g of portion $B_1$ (between $t_R$ and $t_M$) containing 30% of o-DEB, 23% of m-DEB and 47% of p-DEB and 5.90 g of portion $B_2$ (between $t_M$ and $t_C$) containing 1.1% of o-DEB, 0.5% of m-DEB and 98.4% of p-DEB, in the eluation order, were separately obtained.

Then, the portions $B_1$ and $B_2$ obtained above, and 16 g of the fresh starting mixture A were charged to the column in the order of the mixture A and the portions $B_1$ and $B_2$ and, then, developed with the desorbent.

The above-defined times $t_C$ and $t_M$ were redetermined from the chromatogram thus obtained. Thereafter, the same operations were repeated, while the recovery amount of the desired component and the amounts of the portions $B_1$ and $B_2$ in each operation were kept constant. The recovery yields and the purity of the intended component were changed as shown in Table 1 below.

The following results were obtained at a steady state.

$t_C$ = 24.8 min
$t_M$ = 19.8 min
$t_R$ = 18.3 min
$t_P$ = (purity limit = 99%) = 20.6 min
$t_F$ = 14.0 min
$t_E$ = 33.9 min
$W_T$ = 19.9 min
Recovery amount of intended component = 2.8 g Thus, an allowance time $\Delta t$ for cutting the desired component having the desired purity was 4.2 min.

Example 24

Figure 22:
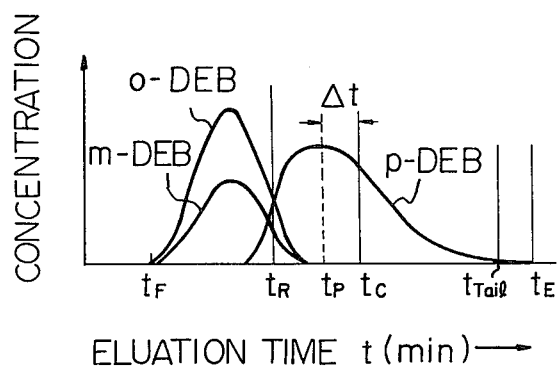

This example was based on the chromatogram of Example 22 after a steady state was obtained. The chromatogram is shown in FIG. 22. The specific points of the chromatogram were as follows.

$t_C$ = 24.8 min (see Example 23)
$t_P$ (purity = 99%) = 21.8 min
$\Delta t$ = 3.0 min
$t_F$ = 14.0 min
$t_E$ = 33.6 min From the chromatogram obtained above, the time at which the portion B should be recharged in the next operation was determined.

$t_R$ (Time before which the concentration of the remaining intended component was zero, in front of $t_C$) = 19.1 min Thus, 12.27 g of portion B (between $t_C$ and $t_R$) containing 16.1% of o-DEB, 12.2% of m-DEB and 71.8% of p-DEB was separately obtained. The tailing portion of the intended component was cut at $t_{Tail}$ = 31.0 min and portion C (between $t_{Tail}$ and $t_E$) was separately obtained without removing the eluent.

Then, the portions B and C, and 16 g of the starting mixture A were charged to the column in the order of C, A and B and then developed with the desorbent.

The above-defined time $t_C$ was redetermined from the chromatogram thus obtained. Thereafter, the same operations were repeated, while the recovery amount of the intended component and the amounts of the portions B and C in each operation were kept constant. The recovery yields and the purity of the intended component were changed as shown in Table 1 below.

The following results were obtained at a steady state.

$t_C$ = 24.8 min
$t_R$ = 19.1 min
$t_{Tail}$ 31.0 min
$t_P$ (purity = 99%) = 21.8 min
$t_F$ = 14.0 min
$t_E$ = 33.6 min
$W_T$ = 19.6 min
Recovery amount of intended component = 2.8 g Thus, an allowance time $\Delta t$ for cutting the intended component having the desired purity was 3.0 min.

As is clear from the results shown in Examples 22 to 24, the present invention can result in the remarkable effects in the chromatographic separation of the diethylbenzene mixture.

Example 25 (Comparative)

Two titanium cylindrical columns each provided with a jacket and liquid distributors and liquid gathering collectors at the top and bottom thereof and each having an inner diameter of 8 mm and a length of 2.5 m were connected to each other with poly (tetrafluoroethylene) pipes each having an inner diameter of 1 mm to provide a chromatographic separation column. The columns were packed with an ion exchange resin, Dowex 50-X8 (available from Dow Chemical Co.). The columns were stabilized at a temperature of 60° C. and, then, a desorbent, water was charged to the columns to condition the filler in the columns. Then, 15 ml of a starting mixture A comprising an aqueous solution, containing 73 g/l (2N) of hydrochloric acid and 59 g/l (1N) of acetic acid, to be separated in the column was downwardly charged to the column by a constant rate pump. Thus, an adsorption band was formed. Subsequently, the desorbent was downwardly charged to the column at a flow rate of 10 cc/min, thereby developing the above-mentioned adsorption band. Eluates discharged from the bottom of the column was collected as fractions at intervals of 30 seconds. Each fraction was quantitatively determined by a refractometer to obtain weight concentrations of the starting components and the desorbent in each sample.

Figure 23:
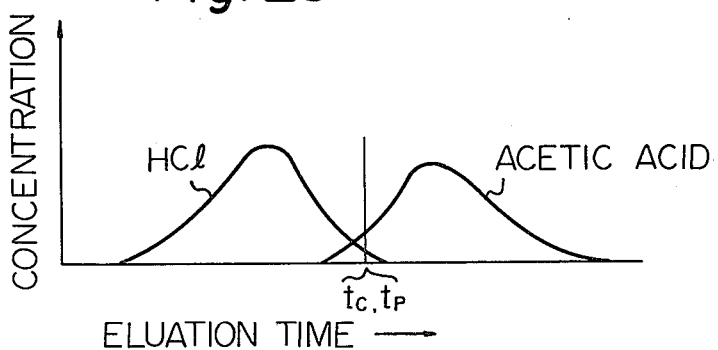

The results are shown in a chromatogram of FIG. 23 in which the abscissa axis represents a time from the initiation of the charge and the development and the ordinate axis represents the concentration of each adsorbed component. From the results of the chromatogram, it was found that the purity of the desired acetic acid component was 98% and the eluation time $t_P$ thereof was 21.5 min.

The time at $t_P$ was fixed and the separation operations were repeated. The recovery yields of the intended component in the starting mixture A and the purities of the recovered intended component were changed as shown in Table 1 below. The average recovery amount of the intended component was 0.80 g.

Example 26

Figure 24:
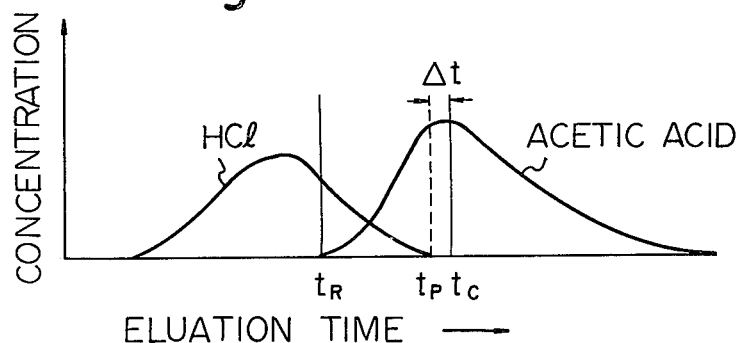
Figure 24:
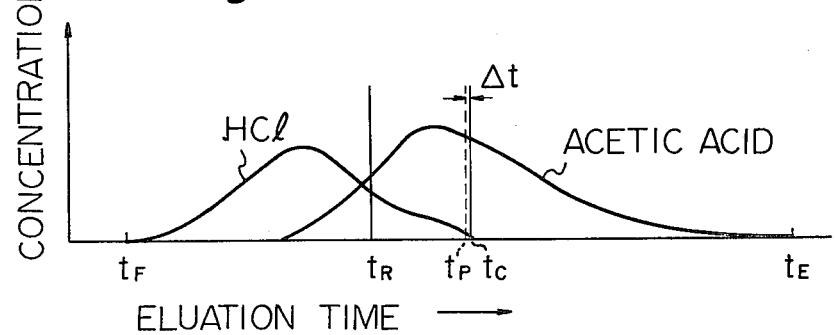

The chromatographic separation was carried out in the same manner as described in Example 25, except that the starting mixture A was previously mixed with 6 ml of 1N acetic acid prior to the charge thereof to the column. The chromatogram thus obtained was shown in FIG. 24a.

From the chromatogram shown in FIG. 24a, a time $t_C$ for which the same amount of the intended component as in Example 25 was recovered was found to be 24.3 min. A time $t_R$ at which the concentration of the remaining intended component was zero was determined from the chromatogram. Thus, 10.1 cc of an aqueous solution containing 68 g/l of hydrochloric acid and 64 g/l of acetic acid was separately obtained as a portion B by effecting the dewatering and concentration until the total concentration of the adsorbates became 132 g/l.

Then, the portion B obtained above and 15 ml of the starting mixture A were charged to the column in such a manner that the portion B was charged subsequent to the starting mixture A, and, then, the adsorption band was developed with the desorbent.

The above-defined times $t_C$ and $t_R$ were redetermined from the chromatogram thus obtained. Thereafter, the same operations were repeated, while the recovery amount of the intended component and the amount of the portion B in each operation were kept constant. Thus, a chromatogram shown in FIG. 24b was obtained. The recovery yields and the purity of the intended component were changed as shown in Table 1 below.

The following results were obtained at a steady state.
$t_C{}^{*1} = 27.8$ min
$t_R = 18.2$ min (see Example 23)
$t_P$ (purity = 98%) = 27.6 min
$t_F = 13.2$ min
$t_E = 33.8$ min
$W_T = 20.6$ min
Recovery amount of intended component = 0.80 g
Allowance time for cutting intended component having desired purity = 0.2 min

*1 Time at which the same amount of the intended component as in Example 25 was obtained.

As is clear from the above results, the present invention could be suitably applied for the separation of an aqueous solution containing inorganic substances. Since the desorbent was contained in the starting mixture at a high concentration, the separation between each peak of the adsorbates was not sharp as compared with other examples and, therefore, the allowance time was not great. However, the effect of the present invention was clearly shown in this Example as compared with Example 25.

TABLE 1

| | | Ex. No. 1 | Ex. No. 2 | Ex. No. 3 |
|---|---|---|---|---|
| Operation conditions et al | Adsorption | 8mmφ × 2.5 mL × 4 (10 m) | Same as left | Same as left |
| | Packing | Potassium exchanged X-type zeolite | " | " |
| | Operation temp. (°C.) | 120 | " | " |
| | Desorbent | Furan | " | " |
| | Composition starting mixture A (%) (* intended component) | PX* (15), EB (20) MX (45), OX (20) | | |
| | Charge volume of mixture A (cc) | 50 cc (0.17 cc/g packing) | | |
| | Composition of previous addition substance | (Conventional method) | 3 g of PX was added to A | Same as left |
| | Flow rate of starting material and desorbing agent (cc/min) | 9.5 cc/min | Same as left | Same as left |
| First developing chromatography | Charge time of desorbent (min) | — | — | — |
| | Chromatogram chart | FIG. 7 | FIG. 8-a | Same as left |
| | $t_2$ (D = desired purity %) (min) | 33.1 (99.5%) | — | — |
| | $\Delta t$ (min) | 0 | — | — |
| | $t_R$ (min) | — | — | — |
| | $t_F$, $t_E$ (min) | — | — | — |
| | $t_M$ (min) | — | — | — |
| | Composition and amount of portion B (%) | — | — | — |
| | Composition and amount of portion B₁ (%) | — | — | — |
| | Composition and amount of portion B₂ (%) | — | — | — |
| | Charge volume of starting mixture A (cc) | — | 50 cc | Same as left |
| | Re-feed method of portion B | — | Mixed with A, all at once | Subsequent to A, all at once |
| | Chromatogram chart | — | FIG. 8-b | FIG. 8 |
| | $t_C$ (min) | — | 39.2 | 38.8 |
| | $t_2$ (P = desired purity %) (min) | — | 37.5 (99.5%) | 36.4 (99.5%) |
| | $\Delta t$ (min) | — | 1.7 | 2.4 |
| | $t_R$ (min) | — | 34.5 | 34.0 |
| Repeated chromatogram at steady state | $t_F$, $t_E$ (WT) (min) | — | 25.0 45.0 (20) | 25.5 44.0 (18.5) |
| | $t_M$ | — | — | — |
| | Composition of portion B (%) | EB (22), PX (78) 11.3 cc (fix) | EB (27), PX (73) 11.3 cc | EB (18), PX (82) 11.3 cc (fix) |
| | Composition of portion B₁ (%) | — | — | — |
| | Composition of portion B₂ (%) | — | — | — |
| | Recovery amount of desired component (g) | 1.5 g | 1.5 g (fix) | 1.5 g (fix) |
| | Recovery rate of desired component (%) in each repeated time in parenthesis | (1) (fix) (2) (3) (4) (5) 23 23 23 23 23 | (1) (fix) (2) (3) (4) (5) 23 23 23 23 23 | (1) (fix) (2) (3) (4) (5) 23 23 23 23 23 |
| | Purity of recovered desired component (%) in each repeated time | 99 95 70 87 92 | 100 100 100 100 100 | 100 100 100 100 100 |
| | Ratio of desorbent used | — | — | — |
| | ATY (g/min cm²) | — | — | — |

| | | Ex. No. |

TABLE 1-continued

| | | 4 | 5 | 6 |
|---|---|---|---|---|
| Operation conditions et al | Adsorption | Same as left | Same as in Ex. 4 | Same as in Ex. 4 |
| | Packing | " | " | " |
| | Operation temp. (°C.) | " | " | " |
| | Desorbent | " | " | " |
| | Composition starting mixture A (%) (* intended component) | " | " | " |
| | Charge volume of mixture A (cc) | Started from steady chromatogram of Ex. 3 | | |
| | Composition of previous addition substance | Same as left | | |
| | Flow rate of starting material and desorbing agent (cc/min) | | | |
| First developing chromatography | Charge time of desorbent (min) | — | Shortened | — |
| | Chromatogram chart | FIG. 9 | FIG. 10 | FIG. 11 |
| | $t_C$ (min) | 38.8 | 38.2 | 38.1 |
| | $t_P$ (D = desired purity %) (min) | 36.4 (99.5%) | 36.4 (99.5%) | 36.4 (99.5%) |
| | $\Delta t$ (min) | 2.4 | 1.8 | 1.7 |
| | $t_R$ (min) | 34.0 | 34.0 | 34.0 |
| | $t_F, t_E$ (min) | 25.5, 44.0 | 25.5, 41.5 | 25.5, 44 |
| | $t_M$ (min) | 36.4 | — | t Tail = 41 (C 41-44 min) |
| | Composition and amount of portion B (%) | — | EB (18), p* (82) 10.5 cc | EB (18), PX (82) 10.2 cc |
| | Composition and amount of portion $B_1$ (%) | EB (37.7), PX (62.3) 5.2 cc | — | — |
| | Composition and amount of portion $B_2$ (%) | EB (0.6), PX (99.4) 6.1 cc | — | — |
| | Charge volume of starting mixture A (cc) | Same as left | 50 cc | Same as left |
| | Re-feed method of portion B | Subsequent to A, $B_1$ and then $B_2$ | Subsequent to A, all at once | Subsequent to C, A and then B |
| | $t_C$ (min) | 38.7 | 38.1 | 38.1 |
| | $t_p$ (P = desired purity %) (min) | 34.4 (99.5%) | 36.2 (99.5%) | 36.4 |
| | $\Delta t$ (min) | 4.3 | 1.9 | 1.7 |
| | $t_R$ (min) | 32.4 | 34.0 | 34.0 |
| Repeated chromatogram at steady state | $t_F, t_E$ (WT) (min) | 25.7 44.1 (18.4) | 25.5 41.5 (16.0) | 25.5 44 (18.5) |
| | $t_M$ | 34.4 | — | (fix) t Tail = 41 (C 41-44 min) |
| | Composition of portion B (%) | — | EB (18), PX (82) 10.5 cc (fix) | EB (18), PX (82) 10.2 cc |
| | Composition of portion $B_1$ (%) | EB (39.3), PX (60.7) 5.2 cc (fix) | — | — |
| | Composition of portion $B_2$ (%) | EB (0.5), PX (99.5) 6.1 cc (fix) | — | — |
| | Recovery amount of desired component (g) | 1.5 g (fix) | 1.5 g (fix) | 1.5 g (fix) |
| | Recovery rate of desired component (%) in each repeated time in parenthesis | (1) (fix) (2) (3) (4) (5) 23 23 23 23 23 | (1) (fix) (2) (3) (4) (5) 23 23 23 23 23 | (1) (fix) (2) (3) (4) (5) 23 23 23 23 23 |
| | Purity of recovered desired component (%) in each repeated time | 100 100 100 100 | 99 99 99 99 | 100 100 100 100 |
| | Ratio of desorbent used | — | EX 5/E5 3 = 0.79 | EX 6/EX 3 = 0.75 |
| | ATY (g/min·cm²) | — | — | — |

*1.96 times of PX concentration in mixture A

TABLE 1-continued

| | | Ex. No. | | |
|---|---|---|---|---|
| | ATY (g/min · cm²) | 0.63 | 0.68 | 0.65 |
| | | 10 | 11 | 12 |
| Operation conditions et al | Adsorption Packing | Same as left | Same as left | Same as left |
| | Operation temp. (°C.) | " | " | " |
| | Desorbent | " | " | " |
| | Composition starting mixture A (%) ("Intended component) | " | " | " |
| | Charge volume of mixture A (cc) | " | 134 cc (0.23 cc/g packing) | " |
| | Composition of previous addition substance | Not mixed with A, but subsequent to A; same comp. as left | Subsequent to A, B₁ and then B₂ | Same as that of Ex. 10, after steady state |
| | Flow rate of starting material and desorbing agent (cc/min) | Same as left | Same as left | Same as left |
| | Charge time of desorbent (min) | " | — | Charge next starting material after 28.8 min |
| First developing chromatography | Chromatogram chart | FIG. 14-a | FIG. 15 | FIG. 16 |
| | $t_C$ (min) | 117.2 | 116.3 | 117.5 |
| | $t_P$ (D = desired purity %) (min) | 111.2 (99.5%) | 110.1 (99.5%) | 114.5 (99.5%) |
| | Δt (min) | 6.0 | 6.2 | 3.0 |
| | $t_R$ (min) | 102.9 | 105. | 105.0 |
| | $t_F, t_E$ (min) | 78, 134 | 78, 136.5 | 78, 130.5 (overlap) |
| | $t_M$ (min) | — | 108.0 | — |
| | Composition and amount of portion B (%) | EB (27.1), PX (72.9) | — | Same as Ex. 10 |
| | Composition and amount of portion B₁ (%) | — | EB (47.4), PX (56.6) 36.3 cc | — |
| | Composition and amount of portion B₂ (%) | — | EB (1.0), PX (99.0) 28.2 cc | — |
| | Charge volume of starting mixture A (cc) | 134 cc | 134 cc | " |
| | Re-feed method of portion B | Subsequent to A, all at once | Subsequent to A, B₁ and then B₂ | |
| Repeated chromatogram at steady state | Chromatogram chart | FIG. 14-b | FIG. 15 | FIG. 16 |
| | $t_C$ (min) | 117.5 (fix) | 116.3 (fix) | Same as Ex. 10 |
| | $t_P$ (P = desired purity %) (min) | 114.5 (99.5%) | 108.8 (99.5%) | " |
| | Δt (min) | 3.0 | 7.5 | " |
| | $t_R$ (min) | 105.0 (fix) | 105.0 (fix) | " |
| | $t_F, t_E$ (WT) (min) | 78, 136.5 (58.5) | 78, 136.5 (58.5) | 78, 130.5 (52.5) |
| | $t_M$ | — | 108.0 (fix) | — |
| | Composition of portion B (%) | EB (27.1), PX (72.9) 64.5 cc | — | Same as Ex. 10 |
| | Composition of portion B₁ (%) | — | EB (57.4), PX (42.6) 30.0 cc | — |
| | Composition of portion B₂ (%) | — | EB (0.8), PX (99.2) 34.5 cc | — |
| | Recovery amount of desired component (g) | 24.8 g | 24.8 g | 24.1 g |
| | Recovery rate of desired component (%) in each repeated time in parenthesis | (1) (2) (3) (4) (5) 100 100 100 100 100 | (1) (2) (3) (4) (5) 100 100 100 100 100 | (1) (2) (3) (4) (5) 97 97 97 97 97 |
| | Purity of recovered desired component (%) in each repeated time | 100 100 100 100 100 | 100 100 100 100 100 | 100 100 100 100 100 |

TABLE 1-continued

|  |  | 13 | 14 | 15 |
|---|---|---|---|---|
|  | Ratio of desorbent used | (Same as left) = 8.5 | (Same as left) = 8.5 | (Same as left) = 7.2 |
|  | ATY (g/min cm²) | 0.84 | 0.84 | 0.91 |
| Operation conditions et al | Adsorption | 20 mmφ × 2.5 mL × 6 (15 m) | 20 mmφ × 2.5 mL × 8 (20 mm) | 200 mmφ × 2.5 mL × 6 (15 m) |
|  | Packing | Same as Ex. 7 | " | Same as Ex. 7 |
|  | Operation temp. (°C.) | " | " | " |
|  | Desorbent | " | " | " |
|  | Composition starting mixture A (%) |  |  |  |
|  | (*Intended component) |  |  |  |
|  | Charge volume of mixture A (cc) | 523 cc (0.19 cc/g packing) | 838 cc (0.23 cc/g packing) | 52.3 l (0.19 cc/g packing) |
|  | Composition of previous addition substance | — | Subsequent to A, 403 cc of B having same comp. as Ex. 9 | — |
|  | Flow rate of starting material and desorbing agent (cc/min) | (conventional method) 52.3 cc/min | Same as Ex. 13 | (conventional method) 5.23 l/min |
| First developing chromatography | Charge time of desorbent (min) |  |  |  |
|  | Chromatogram chart | FIG. 12 | FIG. 14 | FIG. 12 |
|  | $t_C$ (min) | 82.7 | 117.2 | 84.8 |
|  | $t_P$ (D = desired purity %) (min) | 82.7 (99.5%) | 115.8 (99.5%) | 84.8 (99.5%) |
|  | Δt (min) | — | 1.4 | 0 |
|  | $t_R$ (min) | — | 104.7 | — |
|  | $t_F, t_E$ (min) | — | 78, 137.5 | — |
|  | $t_M$ (min) | — | — | — |
|  | Composition and amount of portion B (%) | — | EB (33.3), PX (66.7) | — |
|  | Composition and amount of portion B₁ (%) | — | — | — |
|  | Composition and amount of portion B₂ (%) | — | — | — |
|  | Charge volume of starting mixture A (cc) | 523 cc | 838 cc | 52.3 l |
|  | Re-feed method of portion B | — | Subsequent to A, all at once | — |
| Repeated chromatogram at steady state | Chromatogram chart | FIG. 12 | FIG. 14 | FIG. 12 |
|  | $t_C$ (min) | 82.7 (fix) | 117.2 (fix) | 84.8 (fix) |
|  | $t_P$ (P = desired purity %) (min) | — | 114.3 (99.5%) | — |
|  | Δt (min) | — | 2.9 | — |
|  | $t_R$ (min) | — | 104.7 (fix) | — |
|  | $t_F, t_E$ (WT) (min) | 56.5, 101.0 (44.5) | 77.5, 138.0 (60.5) | 56.5, 99.5 (43.0) |
|  | $t_M$ | — | — | — |
|  | Composition of portion B (%) | — | EB (27.1), PX (72.9) 403 cc | — |
|  | Composition of portion B₁ (%) | — | — | — |
|  | Composition of portion B₂ (%) | — | — | — |
|  | Recovery amount of desired component (g) | 76.5 | 155 g | 6.0 kg |
|  | Recovery rate of desired component (%) in each repeated time in parenthesis | (1) (2) (3) (4) (5)<br>79 81 76 71 82 | (1) (2) (3) (4) (5)<br>100 100 100 100 100 | (1) (2) (3) (4) (5)<br>62 66 54 63 66 |
|  | Purity of recovered desired component (%) in each repeated time | 99.5 96.2 99.3 99.7 97.8 | 100 100 100 100 100 | 99.5 96.1 99.8 99.1 96.2 |

TABLE 1-continued

|  |  | Ex. No. 16 | Ex. No. 17 | Ex. No. 18 |
|---|---|---|---|---|
| Operation conditions et al | Ratio of desorbent used ATY (g/min · cm²) | 0.55 | (Same as left) = 9.8 0.82 | (Same as left) = 20.7 0.44 |
|  | Adsorption | 200 mmφ × 2.5 mL × 8 (20 m) | Same as Ex. 16 | Same as Ex. 17 |
|  | Packing | Same as Ex. 15 | " | " |
|  | Operation temp. (°C.) | " | " | " |
|  | Desorbent | " | " | " |
|  | Composition starting mixture A (%) (*Intended component) | " | " | " |
|  | Charge volume of mixture A (cc) | 83.8 l (0.23 cc/g packing) | " | " |
|  | Composition of previous addition substance | Subsequent to A, 23.2 l of $B_1$ and then 17.1 l of $B_2$, both having same comp. as in Ex. 11 Same as Ex. 15 | " | " |
|  | Flow rate of starting material and desorbing agent (cc/min) |  |  | Next charge after 29 min |
|  | Charge time of desorbent (min) |  |  |  |
| First developing chromatography | Chromatogram chart | FIG. 15 | FIG. 17 | FIG. 18 |
|  | $t_C$ (min) | 117.2 | 117.0 | 117.0 |
|  | $t_P$ (D = desired purity %) (min) | 113.4 (99.5%) | 113.4 (99.5%) | 113.4 (99.5%) |
|  | Δt (min) | 3.8 | 3.6 | 3.6 |
|  | $t_R$ (min) | 103.9 | 103.9 | 103.9 |
|  | $t_F, t_E$ (min) | 77.6, 138.5 | 77.6, 138.5 | 77.6, 136.5 (overlap) |
|  | $t_M$ (min) | 110.0 | 110.0 ($t_{Tail}$ 135 min) | 110.0 ($t_{Tail}$ 135 min) |
|  | Composition and amount of portion B | — | — | — |
|  | Composition and amount of portion $B_1$ (%) | EB (44.8), PX (55.2) 23.7 l | EB (44.8), PX (55.2) 23.7 l | EB (44.8), PX (55.2) 23.7 l |
|  | Composition and amount of portion $B_2$ (%) | EB (1.8), PX (98.2) 16.6 l | EB (1.8), PX (98.2) 16.3 l | EB (1.8), PX (98.2) 16.3 l |
|  | Charge volume of starting mixture A (cc) | 83.8 l (0.23 cc/g filler) | Same as Ex. 16 | Same as Ex. 17 |
|  | Re-feed method of portion B | Subsequent to A, $B_1$ and then $B_2$ | After C, A, $B_1$ and $B_2$ | " |
|  | Chromatogram chart | FIG. 15 | FIG. 17 | FIG. 18 |
|  | $t_C$ (min) | 117.2 (fix) | 117.0 (fix) | " |
|  | $t_P$ (P = desired purity %) (min) | 113.1 (99.5%) | 113.0 (99.5%) | " |
|  | Δt (min) | 4.1 | 4.0 | " |
|  | $t_R$ (min) | 103.9 (fix) | 103.9 (fix) | " |
| Repeated chromatogram at steady state | $t_F, t_E$ (WT) (min) | 77.6, 138.5 (60.9) | 77.6, 138.5 (60.9) | 77.6, 136.5 (58.9) |
|  | $t_M$ | 110.0 (fix) | 110.0 (fix) $t_{Tail}$ 135 min) | Same as Ex. 17 (overlap) |
|  | Composition of portion $B_1$ (%) | EB (45.0), PX (55.0) 23.8 l | EB (45.0), PX (55.0) 23.8 l | Same as Ex. 17 |
|  | Composition of portion $B_2$ (%) | EB (1.3), PX (98.7) 16.5 l | EB (1.3), PX (98.7) 16.2 l | " |
|  | Recovery amount of desired component (g) | 15.5 kg | 15.5 kg | 15.46 kg |
|  | Recovery rate of desired component (%) in each repeated time in parenthesis | (1) (2) (3) (4) (5) 100 100 100 100 100 | (1) (2) (3) (4) (5) 100 100 100 100 100 | (1) (2) (3) (4) (5) 99.7 99.7 99.7 99.7 99.7 |
|  | Purity of recovered desired repeated time | 100 100 100 100 100 | 100 100 100 100 100 | 100 100 100 100 100 |

TABLE 1-continued

| | | Ex. No. | | |
|---|---|---|---|---|
| | | 19 | 20 | 21 |
| | Ratio of desorbent used ATY (g/min cm²) | (Same as left) = 9.0  0.81 | 0.81 | 0.84 |
| Operation conditions et al | Adsorption | Same as Ex. 7 | Same as Ex. 10 | 8 mmφ × 5 mL × 1 |
| | Packing | " | " | Potassium exchange X-type zeolite |
| | Operation temp. (°C.) | 75 | Same as Ex. 19 | 70 |
| | Desorbent | n-propyl ether | Same as Ex. 10 | n-butyl ether |
| | Composition starting mixture A (%) (*Intended component) | Same as Ex. 7 | " | o-DEB (37%) m-DEB (28%) p-DEB* (35%) |
| | Charge volume of mixture A (cc) | " | " | 16 g |
| | Composition of previous addition substance | — | PX (69.0) ⎫ 64.5 cc  EB (31.0) ⎭ (Subsequent to A) | — |
| | Flow rate of starting material and desorbing agent (cc/min) | (conventional method) " | Same as Ex. 10 | (conventional method) 8.44 cc/min |
| | Charge time of desorbent (min) | — | — | — |
| First developing chromatography | Chromatogram chart | FIG. 12 | FIG. 14 | FIG. 19 |
| | $t_C$ (min) | 79.8 | 115.1 | 21.9 (fix) |
| | $t_P$ (D = desired purity %) (min) | 79.8 min (99.5%) | 110.6 (99.5%) | 21.9 (99%) |
| | Δt (min) | 0 | 4.5 | 0 |
| | $t_R$ (min) | — | 101.8 | — |
| | $t_F, t_E$ (min) | — | 77.5, 131 | — |
| | $t_M$ (min) | — | — | — |
| | Composition and amount of portion B (%) | — | EB (31.0) PX (69.0) 64.5 cc | — |
| | Composition and amount of portion.B₁ (%) | — | — | — |
| | Composition and amount of portion.B₂ (%) | — | — | — |
| | Charge volume of starting mixture A (cc) | Same as Ex. 7 | 116.2 cc | — |
| | Re-feed method of portion B | — | Subsequent to A, all at once | — |
| | Chromatogram chart | FIG. 12 | FIG. 14 | — |
| | $t_C$ (min) | 79.8 min (fix) | 115.3 (fix) | — |
| | $t_P$ (P = desired purity %) (min) | — | 114.1 (99.5%) | — |
| | Δt (min) | — | 1.2 | — |
| | $t_R$ (min) | — | 101.0 | — |
| Repeated chromatogram at steady state | $t_F, t_E$ (WT) (min) | 56.6, 98.7 (42.1) | 77.5, 132.3 (54.8) | — |
| | $t_M$ | — | — | — |
| | Composition of portion B (%) | — | EB (31.0), PX (69.0) | — |
| | Composition of portion B₁ (%) | — | — | — |
| | Composition of portion B₂ (%) | — | — | — |
| | Recovery amount of desired component (g) | 12.7 g | 21.5 g | 2.8 g |
| | Recovery rate of desired component (%) in each repeated time in parenthesis | (1) (2) (3) (4) (5)  82 77 89 83 79 | (1) (2) (3) (4) (5)  100 100 100 100 100 | (1) (2) (3) (4) (5)  18 18 18 18 18 |
| | Purity of recovered desired component (%) in each | 99.5 99.8 96.1 98.1 99.7 | 100 100 100 100 100 | 98.0 90.2 86.9 99.7 83.4 |

TABLE 1-continued

|  |  | Ex. No. | | |
|---|---|---|---|---|
|  |  | 22 | 23 | 24 |
|  | repeated time | 15.2 | 9.3 | |
|  | Ratio of desorbent used | 0.60 | 0.78 | |
|  | ATY (g/min · cm²) | | | |
| Operation conditions et al | Adsorption | Same as Ex. 21 | Same as Ex. 21 | Same as Ex. 23 |
|  | Packing | " | " | " |
|  | Operation temp. (°C.) | " | " | " |
|  | Desorbent | " | " | " |
|  | Composition starting mixture A (%) (*Intended component) | " | " | " |
|  | Charge volume of mixture A (cc) | | | |
|  | Composition of previous addition substance | 6.0 g of p-DEB was added to A | Start from steady state in Ex. 22 | |
|  | Flow rate of starting material and desorbing agent (cc/min) | Same as Ex. 21 | Same as Ex. 21 | |
|  | Charge time of desorbent (min) | | | |
| First developing chromatography | Chromatogram chart | FIG. 20-a | FIG. 21 | FIG. 22 |
|  | tC (min) | 23.2 | 24.8 | 24.8 |
|  | tp (D = desired purity %) (min) | — | 21.8 (99%) | 21.8 (99%) |
|  | Δt (min) | — | 3.0 | 3.0 |
|  | tR (min) | — | 19.1 | 19.1 |
|  | tF, tE (min) | — | 14.0, 33.6 (19.6) | 14.0, 33.6 (19.6) |
|  | tM (min) | | 21.6 | (fix) |
|  | Composition and amount of portion B (%) | oDEB (28%), mDEB (21%) pDEB (51%) 12.27 g | | tTail = 31.0 (c 31.0–33.6 min) oDEB (16.1), mDEB (12.2) pDEB (71.8) 12.27 g |
|  | Composition and amount of portion B₁ (%) | — | oDEB (30%), mDEB (23%) pDEB (47%) 6.37 g | — |
|  | Composition and amount of portion B₂ (%) | — | oDEB (1.1%), mPER (0.5%) pDEB (98.4%) 5.90 g | — |
|  | Charge volume of starting mixture A (cc) | Same as Ex. 21 | Same as Ex. 21 | Same as Ex. 21 |
|  | Re-feed method of portion B | Subsequent to A, all at once | Subsequent to A, B₁ and then B₂ | After C, A and then B |
|  | Chromatogram chart | FIG. 20-b | FIG. 21 | FIG. 22 |
|  | tC (min) | 24.8 | 24.8 | 24.8 |
|  | tp (P = desired purity %) (min) | 21.8 (99%) | 20.6 (99%) | 21.8 (99%) |
|  | Δt (min) | 3.0 | 4.2 | 3.0 |
|  | tR (min) | 19.1 | 18.3 | 19.1 |
| Repeated chromatogram at steady state | tF, tE (WT) (min) | 14.0 33.6 (19.6) | 14.0 33.9 (19.9) | 14.0 33.6 (19.6) |
|  | tM | | 19.8 | (fix) |
|  | | | | tTail = 31.0 (c 31.0–33.6 min) |
|  | Composition of portion B (%) | oDEB (16.1), mDEB (12.2) pDEB (71.8) 12.27 g (fix) | — | Same as Ex. 22 |
|  | Composition of portion B₁ (%) | — | oDEB (30), mDEB (23), PDEB (47) 6.37 g (fix) | — |
|  | Composition of portion B₂ (%) | — | oDEB (1.0), mDEB (0.4) pDEB (98.6) 5.90 g (fix) | — |
|  | Recovery amount of desired component (g) | 2.8 g (fix) | 2.8 g (fix) | 2.8 g (fix) |

TABLE 1-continued

| | | (1) (2) (3) (4) (5)<br>18 18 18 18 18 | (1) (2) (3)<br>18 18 | |
|---|---|---|---|---|
| Recovery rate of desired component (%) in each repeated time in parenthesis | | | | |
| Purity of recovered desired component (%) in each repeated time | | 100 100 100 100 100 | 100 100 100 | 100 100 100 100 |
| Ratio of desorbent used | | — | — | — |
| ATY (g/min cm²) | | — | — | Ex. 22/Ex. 24 = 0.86 |

| | | | Ex. No. | |
|---|---|---|---|---|
| | | | 25 | 26 |
| Operation conditions et al | Adsorption | Packing | 8 mmφ × 2.5 m × 2 ion-exchange resin Dowex 50-X8 | Same as Ex. 25 |
| | | Operation temp. (°C.) | 60 | " |
| | | Desorbent | H₂O | " |
| | | Composition starting mixture A (%) (*Intended component) | HCl 2N (73 g/l) acetic acid* 1N (59 g/l) | " |
| | | Charge volume of mixture A (cc) | 15 ml | 6 ml of 1N acetic acid was added to A. |
| | | Composition of previous addition substance | — | Same as Ex. 25 |
| | | Flow rate of starting material and desorbing agent (cc/min) | (conventional method) 10 cc/min | |
| | First developing chromatography | Charge time of desorbent (min) | — | — |
| | | Chromatogram chart | FIG. 23 | FIG. 24-a |
| | | $t_C$ (min) | 21.5 (fix) | 24.3 |
| | | $t_p$ (D = desired purity %) (min) | 21.5 (98%) | — |
| | | Δt (min) | 0 | — |
| | | $t_R$ (min) | — | — |
| | | $t_F$, $t_E$ (min) | — | — |
| | | $t_M$ (min) | — | — |
| | | Composition and amount of portion B (%) | — | — |
| | | Composition and amount of portion B₁ (%) | — | HCl (68 g/l), acetic acid (64 g/l) 10.1 ml/after concentrated to 132 g/l in total |
| | | Composition and amount of portion B₂ (%) | — | — |
| | | Charge volume of starting mixture A (cc) | — | Same as Ex. 25 |
| | | Re-feed method of portion B | — | Subsequent to A, all at once until total amount of solute becomes 132 g/l |
| | Repeated chromatogram at steady | Chromatogram chart | — | FIG. 24-b |
| | | $t_C$ (min) | — | 27.8 |
| | | $t_p$ (P = desired purity %) (min) | — | 27.6 (98%) |
| | | Δt (min) | — | 0.2 |
| | | $t_R$ (min) | — | 18.2 |
| | | $t_F$, $t_E$ (WT) (min) | — | 13.2 33.8 (20.6) |
| | | $t_M$ | — | — |
| | | Composition of portion B (%) | — | HCl(62 g/l), acetic acid (70 g/l) 10.1 ml (fix) after concentrated |

TABLE 1-continued

| state | | |
|---|---|---|
| Composition of portion B₁ (%) | — | — |
| Composition of portion B₂ (%) | — | — |
| Recovery amount of desired component (g) | 0.80 g | 0.80 g |
| Recovery rate of desired component (%) in each repeated time in parenthesis | (1) (2) (3) (4) (5)<br>90 90 90 90 90 | (1) (2) (3) (4) (5)<br>100 100 100 100 100 |
| Purity of recovered desired component (%) in each repeated time | 98.0 90.2 86.9 99.7 83.4 | 100 100 100 100 100 |
| Ratio of desorbent used | — | — |
| ATY (g/min · cm²) | — | to 132 g/l in total |

We claim:

1. An adsorptive separation method comprising alternately supplying a starting mixture A which is a mixture of organic substances and a desorbent into a column packed with an adsorbent, treating to form and move an adsorption band of the starting mixture A and recovering the intended component at a purity higher than the aimed purity from an eluate, wherein after the entire amount of the intended component passing through the column is increased over the amount of the intended component in the starting mixture A and the intended component is separated and recovered, a portion B which is at least a part of the remaining intended component-containing portion and in which the desorbent is separated and removed to a concentration lower than the desorbent concentration in the starting mixture A and the intended component is contained at a concentration higher than the concentration of the intended component in the starting mixture A is mixed with the starting mixture A and supplied to the column or said portion B and the starting mixture A are successively supplied to the column one by one, and then, the desorbent is supplied.

2. An adsorptive separation method according to claim 1, wherein the starting mixture A is substantially free of the desorbent.

3. An adsorptive separation method according to claim 1, wherein the supply of the portion B into the column is carried out sequentially between the supply of the starting mixture A and the supply of the desorbent.

4. An adsorptive separation method according to claim 3, wherein the portion B is divided into at least two parts and the parts of the portion B are independently supplied into the column.

5. An adsorptive separation method accoding to claim 4, wherein the parts of the portion B are supplied into the column in the order of elution.

6. An adsorptive separation method according to claim 1, wherein the supply of the desorbent to be conducted after the starting mixture A and the portion B are supplied to the column in the mixed state or sequentially is carried out while adjusting the amount supplied of the desorbent so that the relatively low concentration portion at the front end part and/or rear end part of the adsorption band is piled on the adjacent adsorption band after movement of a certain distance.

7. An adsorptive separation method according to claim 1, wherein the separation of the intended component is carried out so that a portion C of a mixture of the desorbent and the intended component, which contains the intended component at a low concentration, is not contained in the separated fraction, and said portion C is supplied before or after the adsorbate portion consisting of the starting mixture A and the portion B continuously thereto.

8. An adsorptive separation method according to claim 1, wherein the column has an inner diameter of at least 20 mm and the ratio of the diameter to the particle size of the packed adsorbent of at least 20.

9. An adsorptive separation method according to claim 8, wherein the inner diameter of the column is at least 200 mm.

10. An adsorptive separation method according to claim 1, wherein the adsorbent is a zeolite and the starting mixture A to give the intended component is a hydrocarbon mixture.

11. An adsorptive separation method according to claim 10, wherein the zeolite is a faujasite and the hydrocarbon mixture is a mixture of xylene isomers, and the intended component is p-xylene.

12. An adsorptive separation method according to claim 11, wherein the desorbent is a lower aliphatic ether represented by the following general formula:

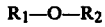

wherein $R_1$ and $R_2$, which may be the same or different, stand for an alkyl group having 3 or 4 carbon atoms, exclusive of an n-butyl group.

13. An adsorptive separation method comprising alternately supplying a starting mixture of xylenes containing p-xylene, m-xylene, o-xylene and ethylbenzene and a desorbent into a column packed with an adsorbent, treating to form and move an adsorption band of the starting mixture of xylenes and recovering the intended component at a purity higher than the aimed purity from an eluate, wherein after the entire amount of the intended component passing through the column is increased over the amount of the intended component in the starting mixture of xylenes and the intended component is separated and recovered, a portion B which is at least a part of the remaining intended component-containing portion and in which the desorbent is separated and removed to a concentration lower than the desorbent concentration in the starting mixture of xylenes and the intended component is contained at a concentration higher than the concentration of the intended component in the starting mixture of xylenes is mixed with the starting mixture of xylenes and supplied to the column or said portion B and the starting mixture of xylenes are successively supplied to the column one by one, and then, the desorbent is supplied.

14. An adsorptive separation method according to claim 13, wherein the intended component is p-xylene.

* * * * *